US012350352B2

(12) United States Patent
Son et al.

(10) Patent No.: US 12,350,352 B2
(45) Date of Patent: *Jul. 8, 2025

(54) COMPOSITION FOR SURFACE MODIFICATION

(71) Applicant: LG Household & Health Care Ltd., Seoul (KR)

(72) Inventors: Seong Kil Son, Daejeon (KR); Kyoung Ran Park, Daejeon (KR); Dong Wan Kim, Daejeon (KR); Kyung Hwan Kim, Daejeon (KR); Ji Hee Yoo, Daejeon (KR); Young Hyun Kim, Daejeon (KR); Jeong Rae Lee, Daejeon (KR); Sang Min Lee, Daejeon (KR)

(73) Assignee: LG Household & Health Care Ltd., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 17/966,148

(22) Filed: Oct. 14, 2022

(65) Prior Publication Data

US 2023/0088314 A1 Mar. 23, 2023

Related U.S. Application Data

(63) Continuation of application No. 16/909,197, filed on Jun. 23, 2020, now Pat. No. 11,612,552, which is a continuation of application No. 15/753,067, filed as application No. PCT/KR2016/009505 on Aug. 26, 2016, now Pat. No. 10,799,436.

(30) Foreign Application Priority Data

| Aug. 27, 2015 | (KR) | 10-2015-0121041 |
|---|---|---|
| Aug. 27, 2015 | (KR) | 10-2015-0121047 |
| Aug. 27, 2015 | (KR) | 10-2015-0121048 |
| Mar. 3, 2016 | (KR) | 10-2016-0025891 |
| Mar. 3, 2016 | (KR) | 10-2016-0025892 |

(51) Int. Cl.

| A61K 8/41 | (2006.01) |
|---|---|
| A61K 8/11 | (2006.01) |
| A61K 8/36 | (2006.01) |
| A61K 8/42 | (2006.01) |
| A61K 8/44 | (2006.01) |
| A61K 8/46 | (2006.01) |
| A61K 8/67 | (2006.01) |
| A61K 8/73 | (2006.01) |
| A61K 8/84 | (2006.01) |
| A61K 8/86 | (2006.01) |
| A61K 8/88 | (2006.01) |
| A61K 8/898 | (2006.01) |
| A61Q 5/00 | (2006.01) |
| A61Q 5/02 | (2006.01) |
| A61Q 5/12 | (2006.01) |
| A61Q 19/00 | (2006.01) |
| A61Q 19/02 | (2006.01) |
| A61Q 19/08 | (2006.01) |
| A61Q 19/10 | (2006.01) |
| C11D 3/00 | (2006.01) |
| C11D 3/26 | (2006.01) |
| C11D 3/37 | (2006.01) |

(52) U.S. Cl.
CPC ............... *A61K 8/11* (2013.01); *A61K 8/36* (2013.01); *A61K 8/41* (2013.01); *A61K 8/42* (2013.01); *A61K 8/44* (2013.01); *A61K 8/466* (2013.01); *A61K 8/675* (2013.01); *A61K 8/735* (2013.01); *A61K 8/736* (2013.01); *A61K 8/84* (2013.01); *A61K 8/86* (2013.01); *A61K 8/88* (2013.01); *A61K 8/898* (2013.01); *A61Q 5/00* (2013.01); *A61Q 5/02* (2013.01); *A61Q 5/12* (2013.01); *A61Q 19/00* (2013.01); *A61Q 19/02* (2013.01); *A61Q 19/08* (2013.01); *A61Q 19/10* (2013.01); *C11D 3/00* (2013.01); *C11D 3/26* (2013.01); *C11D 3/3703* (2013.01); *C11D 3/3707* (2013.01); *C11D 3/3719* (2013.01); *A61K 2800/88* (2013.01); *A61K 2800/94* (2013.01)

(58) Field of Classification Search
None
See application file for complete search history.

(56) References Cited

U.S. PATENT DOCUMENTS

| 6,121,406 A | 9/2000 | Imashiro et al. |
|---|---|---|
| 10,799,436 B2 | 10/2020 | Son et al. |

(Continued)

FOREIGN PATENT DOCUMENTS

| EP | 2256142 A1 | 12/2010 |
|---|---|---|
| JP | 20007642 A | 1/2000 |

(Continued)

OTHER PUBLICATIONS

International Search Report From PCT/KR2016/009505 dated Jan. 18, 2017.

(Continued)

*Primary Examiner* — Katherine Peebles
(74) *Attorney, Agent, or Firm* — Lerner David LLP

(57) ABSTRACT

The present invention relates to a composition for surface modification. The composition for surface modification according to the present invention contains a particular carbodiimide-based compound, thus forms a covalent bond without damaging skin, hair, or fabric, and semipermanently provides desired skin or hair surface modification effects or fabric care effects.

20 Claims, No Drawings

(56) References Cited

U.S. PATENT DOCUMENTS

| | | | |
|---|---|---|---|
| 11,612,552 B2* | 3/2023 | Son | A61K 8/898 424/70.1 |
| 11,975,091 B2* | 5/2024 | Son | A61K 8/8129 |
| 2005/0050656 A1 | 3/2005 | Huang et al. | |
| 2008/0053835 A1 | 3/2008 | Kobata | |
| 2011/0021679 A1 | 1/2011 | Takahashi et al. | |

FOREIGN PATENT DOCUMENTS

| | | |
|---|---|---|
| JP | 20040182731 A | 7/2004 |
| JP | 2009-235278 A | 10/2009 |
| KR | 2002-0068427 A | 8/2002 |
| KR | 2008-0064467 | 1/2014 |
| KR | 10-1453216 B1 | 10/2014 |
| KR | 10-1453220 B1 | 10/2014 |
| KR | 2015-0010549 A | 1/2015 |
| KR | 2015-0066826 A | 6/2015 |
| WO | 2015093517 A1 | 6/2015 |
| WO | 2017117522 A1 | 7/2017 |
| WO | 2017117526 A1 | 7/2017 |
| WO | 2017117543 A1 | 7/2017 |
| WO | 2017117552 A1 | 7/2017 |

OTHER PUBLICATIONS

English Abstract of WO 2015/093517 (Sumitomo Chemical Co.), Japan, Jun. 25, 2015. "Aqueous emulsion showing high adhesion, aqueous adhesive, and laminate", XP002787520, Database accession No. 2015:1054541.

European Search Report From PCT/KR2016/009505 dated Jan. 23, 2019.

* cited by examiner

COMPOSITION FOR SURFACE MODIFICATION

CROSS-REFERENCE TO RELATED APPLICATIONS

This application is a continuation of U.S. application Ser. No. 16/909,197 filed on Jun. 23, 2020, which is a continuation of U.S. application Ser. No. 15/753,067, filed on Feb. 15, 2018 and issued as U.S. Pat. No. 10,799,436 on Oct. 13, 2020, which is a national phase entry under 35 U.S.C. § 371 of International Application No. PCT/KR2016/009505, filed on Aug. 26, 2016, which claims priority to Korean Patent Application Nos. 10-2015-0121041, 10-2015-0121047 and 10-2015-0121048, filed on Aug. 27, 2015 and Korean Patent Application Nos. 10-2016-0025891 and 10-2016-0025892, filed on Mar. 3, 2016, all the disclosures of which are incorporated herein by reference.

TECHNICAL FIELD

The present invention relates to a composition for skin or hair surface modification and a composition for fabric care.

BACKGROUND ART

Cosmetics and personal care products for skin are products which impart skin conditioning effects, such as softness, moisture, smoothness, elasticity, and the like, which are cosmetically advantageous to skin or have functions of preventing a wrinkle, whitening, blocking ultraviolet rays, antioxidation, imparting fragrance, keratin care, preventing or improving itching, stimulating hair growth, preventing acne and inhibiting bacteria, suppressing body odor, atopic dermatitis care, pore care, improving roughness, improving skin tone, improving blood circulation and stimulating blood flow, stimulating penetration of active ingredients and improving a retention time thereof, removing an odor, deodorizing, epilation, dyeing or tattooing with a dye and a powder, fingernail and toenail care, bioconjugation, or the like, and may further provide functions of cleansing, washing, or the like. Research has been conducted on various methods for enhancing the conditioning effects of the cosmetics and personal care products for skin, and although the products have excellent conditioning effects, the effects are mostly only temporary.

Therefore, research for not temporarily but semi-permanently keeping conditioning effects on skin is being actively conducted.

Generally, the human's hair cuticle consists of flat overlapping cells (scales). The cuticle cells are attached at the root of the hair and grow toward the tip of the hair like tiles on a roof. Each cuticle layer has a thickness of about 0.3 to 0.5 μm, and about 5 to 10 μm of the layer is visible. The cuticle in human hair is generally formed with 5 to 10 layers. Each cuticle cell in a hair consists of a cell membrane complex and various sublamellar layers such as the epicuticle, A-layer, exocuticle, endocuticle, and inner layer. The outermost layer, the epicuticle, is covered with lipids (fatty acids) covalently bonded thereto, and 18-methyleicosanoic acid (18-MEA) is the most abundant component thereof. This layer constitutes an outer β-layer of the cell membrane complex in the cuticle, and serves to provide lubrication, decrease friction, and form a hydrophobic surface.

In a hair, a portion that extends above the scalp is referred to as the hair shaft and is affected by the lifespan and length of a hair. Also, the hair shaft is affected by environmental stresses such as dryness, ultraviolet rays, seawater, calcareous components in a pool, and the like, and stresses on hair when hair is cut, shampooed, dried using a hair dryer, combed, permed, or colored. In particular, the hair cuticle making up the outer part of the hair shaft is damaged by the accumulation of more than one of such stresses, even when it is not under the direct influence of such stresses. A damaged hair is in a state in which the hair cuticle is jagged or partially peeled off and detached to some extent. Such a hair loses its gloss and smoothness because it reflects light diffusely. More progressed damage to a hair leads to complete loss of a hair cuticle layer so that the cortex in the hair is exposed, and thus a hair is split or easily broken.

Various treatments have been attempted to improve the surface of hair having damaged 18-MEA. In particular, products providing a hair surface modification effect (i.e., a hair reinforcement effect) such as hair manicure or hair essences by which a hair surface is coated with a silicone are sold or practiced in beauty salons. Particularly, various products which impart a reinforcing effect to hair by coating a hair surface or allowing amino acids to penetrate into the inside of hair, such as reinforcing shampoo and the like, have been developed in recent years.

However, when hair is treated with such a hair-modifying component, it only provides a temporary and short-term effect until the next wash, and thus there is always the inconvenience of re-treating the hair with the hair-modifying component after wash. Therefore, research has been conducted on various methods for enhancing conditioning effects of the cosmetics and personal care products for hair, and although the products have excellent conditioning effects, the effects are mostly only temporary.

Generally, fabric care refers to functions of imparting a softening effect to a fabric, preventing damage caused by light, suppressing formation of a wrinkle in a fabric, allowing the formed wrinkle to be easily removed, vivifying the original color of a fabric, maintaining the original feeling of color thereof for a long time, allowing surface contamination to be easily removed, imparting fragrance, removing an odor, repelling bacteria or pests, preventing damage caused by washing, preventing the penetration of rain, and the like.

A composition for fabric care may commonly include a composition with functions advantageous to a fabric such as washing, regulating, or pointing of a fabric, or the like and a composition with functions advantageous to a fabric such as dyeing, bleaching, softening, or sterilization of a fabric, blocking ultraviolet rays, applying a fragrance to a fabric, or the like for caring a fabric.

Examples of a product prepared by formulating such a composition include a detergent, a softener, a fabric rinse, a treatment, a partially treating agent, and the like.

Examples of a raw material commonly used to constitute such a composition for fabric care include an oil-soluble raw material such as oils and fats, waxes, hydrocarbon, higher fatty acids, higher alcohols, ester oils, silicone oils, and the like, a polymer compound used as an anionic, cationic, amphoteric, or nonionic surfactant, a moisturizer, a thickener, or a film former, a ultraviolet ray absorbent and a ultraviolet ray blocker, an antioxidant, a chelating agent, an ion exchanger, a builder, a bleaching agent, an enzyme, a foam controlling agent, a fluorescence brightening agent, a dye migration proofing agent, a coloring material such as a dye or a pigment, a fragrance, a preservative, and the like.

In addition, as a fabric care component for providing a specific functionality, a component for imparting a softening effect to a fabric, preventing damage caused by light, suppressing formation of a wrinkle in a fabric, allowing the formed wrinkle to be easily removed, vivifying the original color of a fabric, maintaining the original feeling of color thereof for a long time, allowing surface contamination to be easily removed, imparting fragrance, removing an odor, repelling bacteria or pests, preventing damage caused by washing, preventing penetration of rain or the like, or the like may be included in the composition for fabric care. Specifically, the fabric care component may be a soap, an alkylbenzene sulfonate, an alkane sulfonate, an alpha-olefin sulfonate, an alpha-sulfo fatty acid ester, an alkyl sulfate, an alkyl ether sulfate, an alcohol ethoxylate, an alkylphenol ethoxylate, a fatty acid alkanolamide, an alkylamine oxide, a methylglucamide, an alkyl polyglucoside, distearyl dimethyl ammonium chloride, an imidazolium derivative, alkyl dimethylbenzene ammonium chloride, an esterquat, an amino ester salt, an alkyl betaine, an alkyl sulfobetaine, sodium carbonate, calcium carbonate, sodium silicate, sodium triphosphate, nitrotriacetic acid, a polycarboxylate, a zeolite, sodium polycarboxylate, sodium polyacrylate, sodium hydroxyethane diphosphate, sodium perborate, sodium percarbonate, peroxide, hypochlorite, tetraacetylethylenediamine, sodium p-nonanoyloxybenzenesulfonate, sodium percarbonate, a sodium perborate, a protease, a lipase, a starch degrading enzyme, a pectinase, a cellulase, carboxymethyl cellulose, carboxy methyl starch, a cellulose ether, a polyethylene terephthalate/polyoxyethylene terephthalate copolymer, a fatty acid amide, a fatty acid alkanolamide, an amine oxide, stilbene, coumarin, bisbendazole, distyrylbiphenyl, polyvinylpyrrolidone, a polyvinylpyridine oxide, a fragrance, a cyclodextrin, sodium sulfate, a silicone or a derivative thereof, an alkylamine, a fatty alcohol, a fatty acid, polyethylene, magnesium chloride, calcium chloride, sodium chloride, and sodium acetate, or the like.

However, when a fabric is treated with such a fabric care component, it only provides a temporary and short-term effect until the next wash, and thus there is always the inconvenience of re-treating the fabric with the hair-modifying component after wash.

In Japanese Laid-Open Patent Application No. 2004-182731, a cosmetic treatment method for maintaining long-lasting cosmetic characteristics in hair, which has a composition similar to that of skin or a wool fabric, is disclosed. In this technology, a process of primarily activating hair through a physical method using heat, electromagnetic waves, electric fields, sound waves, plasma, or the like, which causes a change in a hair surface, or a chemical method excluding reduction should be performed before hair is subjected to cosmetic treatment. However, in the process of activating hair, high energy such as heat, electromagnetic waves, electric fields, sound waves, plasma, or the like needs to be applied to hair, an oxidizing agent such as hydrogen peroxide, bromate, and the like used as a material for chemical deactivation other than reduction causes severe damage to hair, and polyamines or polysaccharide polymers other than the oxidizing agent may be able to activate hair but are not covalently bonded with hair while activating hair and thus are easily removed by washing.

In Korean Unexamined Patent Publication No. 2008-0064467, a non-aqueous personal care product for skin or hair is disclosed. In the personal care product for skin or hair which consists of a non-aqueous part and an aqueous part, the non-aqueous part includes a hair surface-modifying component having one or more selected from the group consisting of functional groups capable of covalently bonding with a protein residue in a hair or skin surface, such as carbonates, aldehydes, propionaldehyde, butylaldehyde, nitrophenyl carbonate, aziridines, isocyanate, thiocyanate, epoxides, tresylates, succinimide, hydroxysuccinimidyl esters, imidazole, oxycarbonylamidazole, imines, thiols, vinylsulfone, ethyleneimine, thioethers, acrylonitrile, acrylic or methacrylic acid ester, disulfides, ketones, and functional groups represented as RX (here, R is any one selected from the group consisting of alkyls, aryls, aralkyls, rings, and unsaturated rings, and X is I, Br, or Cl), and the non-aqueous part and the aqueous part are mixed immediately before using the product. However, various functional groups as described above are harmful to humans, or target, among amino acids of proteins constituting hair or skin, lysine contained in a small amount in hair and skin keratin (1.9 to 3.1% in hair and 3.1 to 6.9% in skin keratin) or cysteine contained in a small amount in hair and skin keratin (16.6 to 18% in hair and 2.3 to 3.8% in skin keratin) to participate in a reaction. Therefore, reaction efficiency is degraded, and each material needs to be synthesized separately.

In Korean Unexamined Patent Publication No. 2002-0068427, a method of using chitosan as an antibacterial component and adding a microencapsulated fragrance to impart long-lasting fragrance and an antibacterial effect to a fabric in addition to softening a fabric is contemplated. When a fragrance is microencapsulated as described above, the capsule protects the fragrance of a core material from an external environment and improves storage stability of the same, and thus the fragrance of a fabric persists longer. However, since the fragrance capsules also do not remain on a fabric surface and most of them are washed away during a washing process, there are a limitation in providing such effects using only the remaining capsule components in a fabric and an economical problem in which most of the capsules thus used fail to exert their functions and are rinsed by rinsing water.

DISCLOSURE

Technical Problem

It is an aspect of the present invention to provide a composition for skin surface modification capable of semi-permanently and continuously imparting a surface modification effect without causing damage to skin.

It is another aspect of the present invention to provide a composition for hair surface modification capable of semi-permanently and continuously imparting a surface modification effect without causing damage to hair.

It is still another aspect of the present invention to provide a composition for fabric care capable of semi-permanently and continuously imparting a fabric care effect without causing damage to a fabric.

In order to accomplish the above objectives, according to an embodiment of the present invention, there is provided a composition for skin modification, which includes a carbodiimide-based compound represented by Chemical Formula 1 below; and a skin-modifying component:

[Chemical Formula 1]

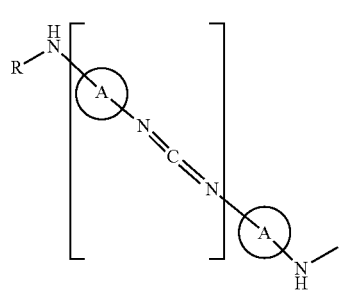

In Chemical Formula 1, A represents a monomer which is one or more selected from structures listed below and has * denoting a connecting position at both termini of a repeat unit thereof, wherein the two As are homopolymers with the same structure or heteropolymers with mutually different structures, R represents hydrogen; C1 to C500 linear, branched, or cyclic hydrocarbon; or aromatic hydrocarbon, wherein a portion of the hydrocarbon molecule includes a double bond, is substituted with one or more elements selected from the group consisting of O, N, S, P, and Si, is substituted in an anionic, cationic, or amphoteric form, or is bonded with a metal ion in a salt form, and m is an integer ranging from 1 to 100.

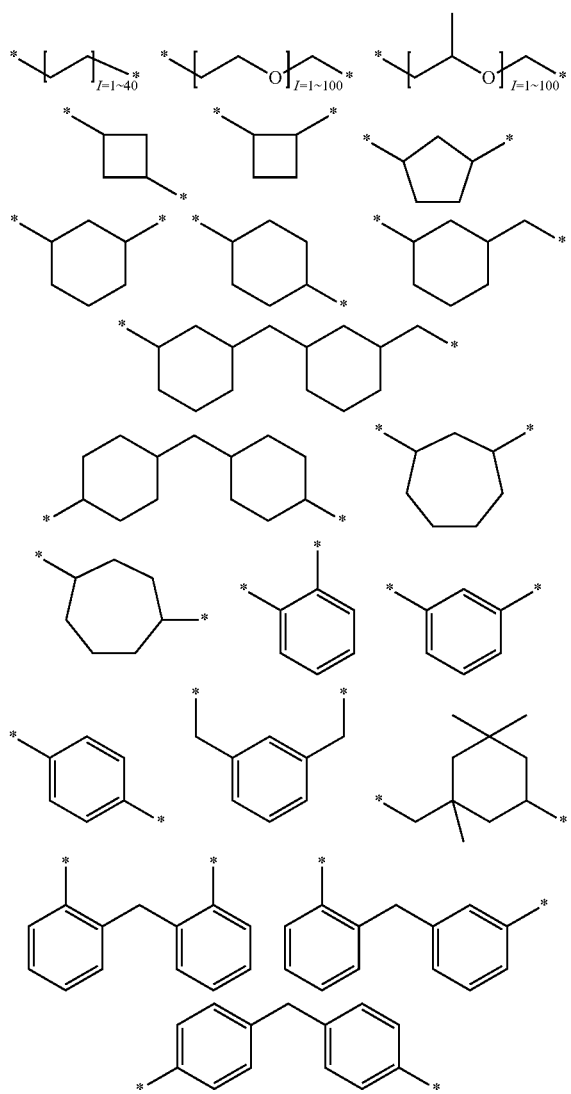

According to another embodiment of the present invention, there is provided a skin care product including the composition for skin surface modification.

According to still another embodiment of the present invention, there is provided a composition for hair modification, which includes a carbodiimide-based compound represented by Chemical Formula 1 below; and a hair-modifying component:

[Chemical Formula 1]

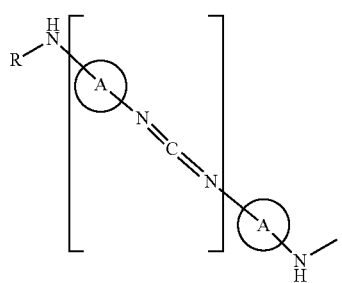

In Chemical Formula 1, A represents a monomer which is one or more selected from structures listed below and has * denoting a connecting position at both termini of a repeat unit thereof, wherein the two As are homopolymers with the same structure or heteropolymers with mutually different structures, R represents hydrogen; C1 to C500 linear, branched, or cyclic hydrocarbon; or aromatic hydrocarbon, wherein a portion of the hydrocarbon molecule includes a double bond, is substituted with one or more elements selected from the group consisting of O, N, S, P, and Si, is substituted in an anionic, cationic, or amphoteric form, or is bonded with a metal ion in a salt form, and m is an integer ranging from 1 to 100.

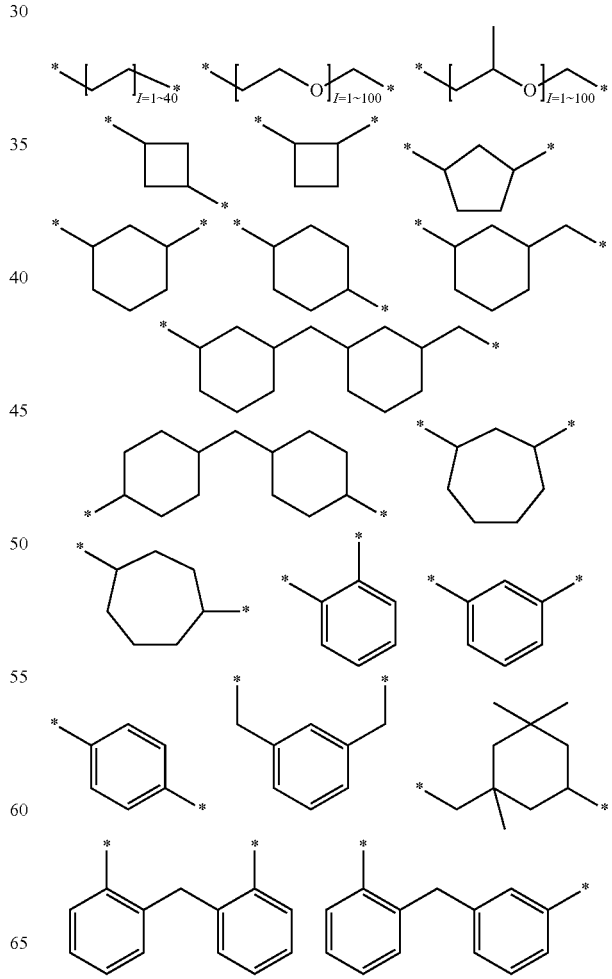

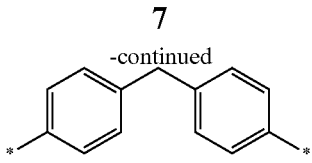

According to yet another embodiment of the present invention, there is provided a hair care product including the composition for hair surface modification.

According to yet another embodiment of the present invention, there is provided a composition for fabric care, which includes a carbodiimide-based compound represented by Chemical Formula 1 below; and a fabric care component:

[Chemical Formula 1]

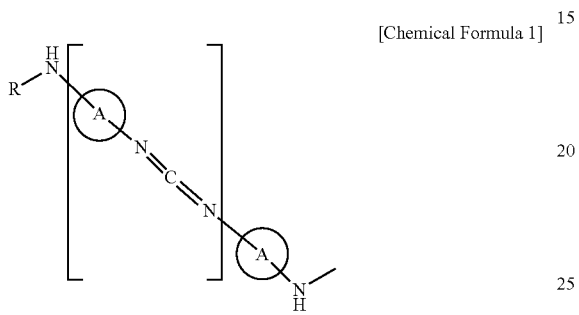

In Chemical Formula 1, A represents a monomer which is one or more selected from structures listed below and has * denoting a connecting position at both termini of a repeat unit thereof, wherein the two As are homopolymers with the same structure or heteropolymers with mutually different structures, R represents hydrogen; C1 to C500 linear, branched, or cyclic hydrocarbon; or aromatic hydrocarbon, wherein a portion of the hydrocarbon molecule includes a double bond, is substituted with one or more elements selected from the group consisting of O, N, S, P, and Si, is substituted in an anionic, cationic, or amphoteric form, or is bonded with a metal ion in a salt form, and m is an integer ranging from 1 to 100.

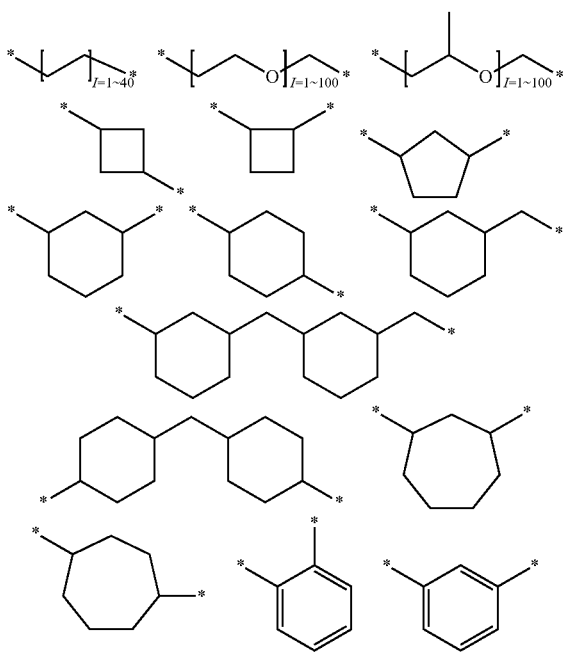

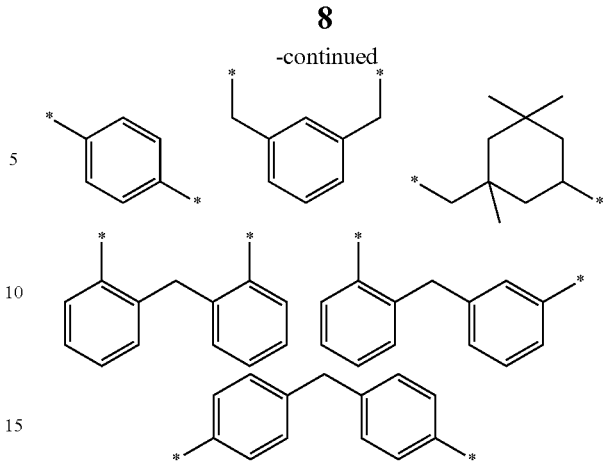

According to yet another embodiment of the present invention, there is provided a fabric care product including the composition for fabric care.

Technical Solution

Hereinafter, the present invention will be described with reference to examples and comparative examples in detail. However, the present invention is not limited to these examples.

The present invention relates to a composition for surface modification which includes a carbodiimide-based compound and a surface-modifying component.

The surface-modifying component is a skin surface-modifying component, a hair surface-modifying component, or a fabric surface-modifying component (fabric care component).

The term "skin" used herein refers to a tissue covering the body, and generally includes facial skin, the scalp, body skin, fingernails and toenails which are accessory organs of the skin, and the like.

The composition for skin surface modification according to the present invention may maximize a skin surface modification effect by forming covalent bonds with proteins in the skin without causing damage to skin, for example, as mediated by a reactive skin surface-modifying component bonded with a carbodiimide group which is formed by reacting a conventionally known skin surface-modifying component with a carbodiimide-based compound.

The composition for hair surface modification according to the present invention may maximize a hair surface modification effect by forming covalent bonds with proteins in the hair, for example, as mediated by a reactive hair surface-modifying component bonded with a carbodiimide group which is formed by reacting a conventionally known hair surface-modifying component with a carbodiimide-based compound.

The composition for fabric surface modification (composition for fabric care) according to the present invention may maximize a fabric care effect by forming covalent bonds with proteins in the fabric, for example, as mediated by a reactive fabric care component bonded with a carbodiimide group which is formed by reacting a conventionally known fabric care component with a carbodiimide-based compound.

The carbodiimide-based compound generally refers to a compound having a structure represented by Chemical Formula 1 below in a molecule thereof:

[Chemical Formula 1]

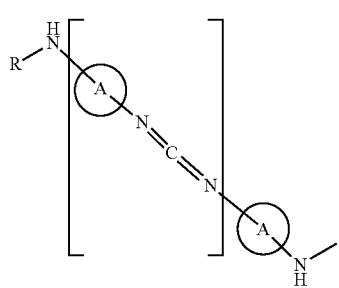

In Chemical Formula 1, m is an integer ranging from 1 to 100, A represents a monomer which is one or more selected from structures listed below and has * denoting a connecting position at both termini of a repeat unit thereof, wherein the two As are homopolymers with the same structure or heteropolymers with mutually different structures, and R represents hydrogen; C1 to C500 linear, branched, or cyclic hydrocarbon; or aromatic hydrocarbon, wherein a portion of the hydrocarbon molecule includes a double bond, is substituted with one or more elements selected from the group consisting of O, N, S, P, and Si, is substituted in an anionic, cationic, or amphoteric form, or is bonded with a metal ion in a salt form, but the present invention is not limited thereto. The cyclic hydrocarbon may include a structure including one or more elements selected from the group consisting of O, N, and Si and/or a double bond in a ring.

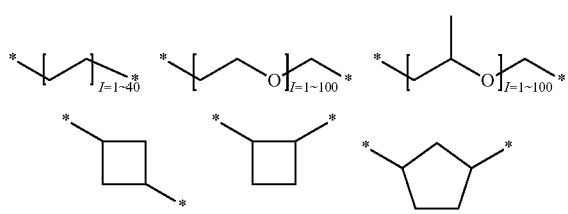

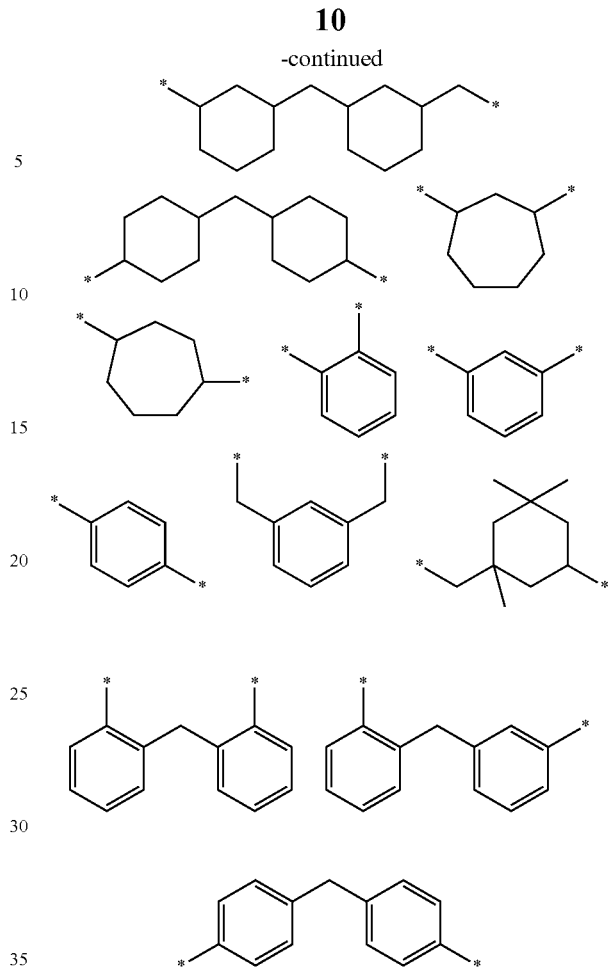

In the present invention, a preferable example of the carbodiimide-based polymer may be a carbodiimide-based compound represented by Chemical Formula 2 below in which the terminal of the polymer is blocked with polyethylene glycol or polypropylene glycol.

[Chemical Formula 2]

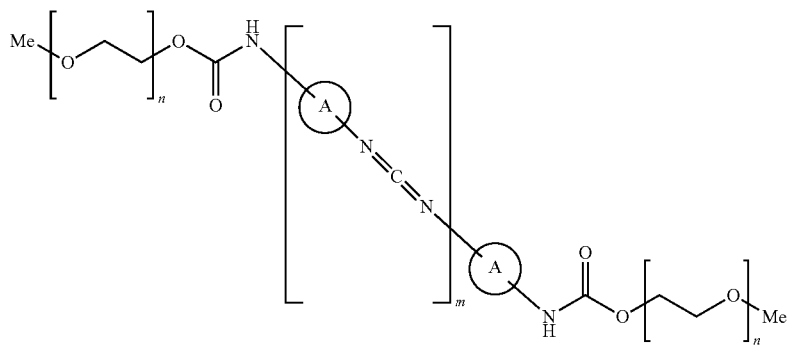

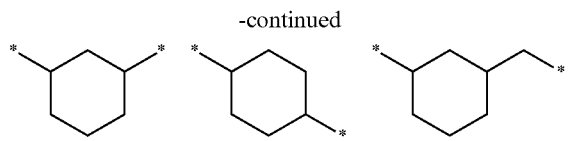

In Chemical Formula 2, A represents a monomer which is one or more selected from structures listed below and has * denoting a connecting position at both termini of a repeat unit thereof, wherein the two As are homopolymers with the same structure or heteropolymers with mutually different structures, m is an integer ranging from 1 to 100, and n is an integer ranging from 1 to 1,000.

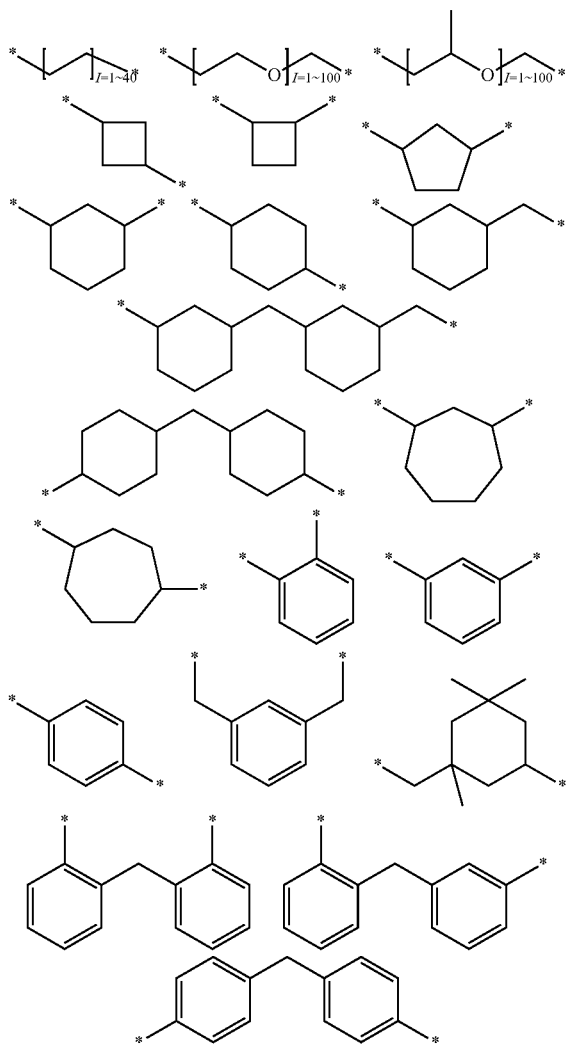

In the present invention, a more preferable example of the carbodiimide-based polymer may be a carbodiimide-based compound represented by Chemical Formula 3 below.

[Chemical Formula 3]

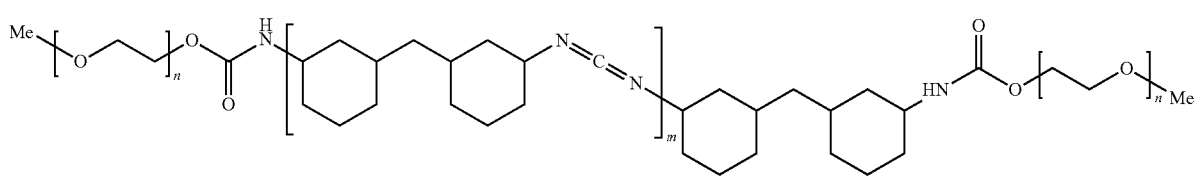

In Chemical Formula 3, n is an integer ranging from 1 to less than 120 (preferably an integer ranging from 1 to less than 100, and more preferably an integer ranging from 1 to less than 70), and m is an integer ranging from 1 to less than 100 (preferably an integer ranging from 1 to less than 30, and more preferably an integer ranging from 1 to less than 10).

In the present invention, the most preferable example of the carbodiimide-based polymer may be 1,1'-methylene-bis-(3-isocyanatocyclohexane)-, homopolymer, and polyethylene glycol mono-Me-ether-blocked, which is a carbodiimide-based compound represented by Chemical Formula 3 in which m is an integer ranging from 1 to 7 and n is an integer ranging from 5 to 50.

In Chemical Formula 1, when there are more than 100 carbodiimide groups in one molecule, the viscosity of a raw material becomes too high, and the molecule has an excessively large molecular weight and too many reaction sites. In addition, since the size of the molecule having carbodiimide groups becomes excessively large, a portion in the molecule exhibiting a substantial functionality is blocked, and thus efficiency is degraded.

In the present invention, specific examples of the carbodiimide-based compound include 1,1'-methylene-bis-(4-isocyanatocyclohexane)-, homopolymer, polyethylene glycol mono-Me-ether-blocked; 1,1'-methylene-bis-(3-isocyanatocyclohexane)-, homopolymer, polyethylene glycol mono-Me-ether-blocked; 1,1'-methylene-bis-(4-isocyanatocycloheptane)-, homopolymer, polyethylene glycol mono-Me-ether-blocked; 1,1'-methylene-bis-(3-isocyanatocycloheptane)-, homopolymer, polyethylene glycol mono-Me-ether-blocked; 1,1'-methylene-bis-(3-isocyanatocyclopentane)-, homopolymer, polyethylene glycol mono-Me-ether-blocked; 1,3-bis(isocyanatomethyl)cyclohexane-homopolymer, polyethylene glycol mono-Me-ether-blocked; benzene-1,3-diisocyanate-, homopolymer, polyethylene glycol mono-Me-ether-blocked; hexamethylene diisocyanate-, homopolymer, polyethylene glycol mono-Me-ether-blocked; PEG 600 diisocyanate-, homopolymer, polyethylene glycol mono-Me-ether-blocked; diphenylmethane-2,2'-diisocyanate-, homopolymer, polyethylene glycol mono-Me-ether-blocked; isophorone diisocyanate-, homopolymer, polyethylene glycol mono-Me-ether-blocked; and the like, but the present invention is not limited thereto.

| Compound | Structure of A in Chemical Formula 2 |
|---|---|
| 1,3-Bis(isocyanatomethyl)cyclohexane-, homopolymer, polyethylene glycol mono-Me-ether-blocked | 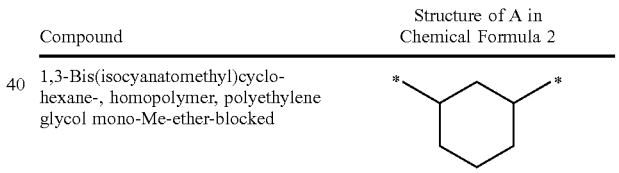 |

-continued

| Compound | Structure of A in Chemical Formula 2 |
|---|---|
| Benzene-1,3-diisocyanate-, homopolymer, polyethylene glycol mono-Me-ether-blocked | 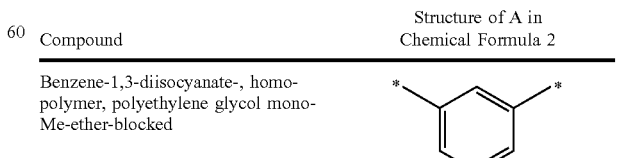 |

-continued

| Compound | Structure of A in Chemical Formula 2 |
|---|---|
| Hexamethylene diisocyanate-, homopolymer, polyethylene glycol mono-Me-ether-blocked | *-(CH₂)₆-* |
| PEG 600 diisocyanate-, homopolymer, polyethylene glycol mono-Me-ether-blocked | *-(CH₂-CH₂-O)_{l=1~100}-* |
| Diphenylmethane-2,2'-diisocyanate-, homopolymer, polyethylene glycol mono-Me-ether-blocked | (diphenylmethane structure) |
| Isophorone diisocyanate-, homopolymer, polyethylene glycol mono-Me-ether-blocked | (isophorone structure) |

The carbodiimide-based compound may be used at a content of 0.0001 to 10 parts by weight, 0.001 to 7 parts by weight, or 0.01 to 5 parts by weight with respect to 100 parts by weight of the entire cosmetic composition. When the content of the carbodiimide-based compound is less than 0.0001 parts by weight, it is difficult for a surface modification effect to persist, and when the content thereof is greater than 10 parts by weight, an excess number of carbodiimide-based compounds as compared to the number of reaction sites in skin reacts with an effective ingredient and not with the skin and thus may act as a component which does not help improve persistence and is lost.

The term "skin surface modification" used herein refers to changing the properties of a skin surface by applying a composition to the skin. The composition may serve to remove dead skin cells or prevent keratinization by coating skin or bonding an active ingredient with skin so as to improve roughness of a skin surface; improve blood circulation or stimulate blood flow so as to make the skin look bright (skin tone improvement); impart beneficial properties to skin through conditioning effects including supplementing nutrition to skin and scalp and imparting elasticity, softness, smoothness, and the like to skin so as to beautify the skin, increase attractiveness, and change an appearance; impart a fragrance or suppress body odor; prevent or improve skin trouble such as itching, atopic dermatitis, and the like; stimulate hair growth; prevent acne; tighten pores; stimulate the penetration of an active ingredient; improve a retention time of an active ingredient; moisturize the skin; or block ultraviolet rays to keep the skin healthy, and may be applied to the skin, scattered on the skin, or used by other similar methods. For example, skin surface modification effects of improving a skin wrinkle, enhancing moisture in skin, supplying nutrition to skin, maintaining skin water homeostatic, removing and reducing dead skin cells, preventing skin trouble, preventing skin aging, skin antioxidation, preventing scalp dandruff, stimulating skin blood circulation, maintaining and improving skin gloss and elasticity, preventing rough skin and chapped skin, and the like may be exhibited.

The term "hair surface modification" used herein refers to changing the properties of a hair surface by applying a composition to the hair. A composition changes the properties of a hair surface by coating hair or bonding an active ingredient with hair, and thus may serve to impart beneficial properties to hair through conditioning effects such as making hair appear thick, improving split and damaged hair, preventing hair from being split or broken, reinforcing tensile strength, enhancing thickness, hair enrichment, supplying nutrition, enhancing elasticity and gloss, moisturizing, preventing damage, repairing damage, dyeing, bleaching, styling, decreasing friction, perming, removing chlorine, removing saltiness, preventing static electricity, decreasing porosity, volumizing, reducing fuzziness, strengthening curls, forming a film and a thin film, softening, eliminating frizz, enhancing smoothness, and the like so as to beautify the hair, increase attractiveness, and change an appearance; moisturizing the hair; or block ultraviolet rays to keep the hair healthy, and may be applied to the hair, scattered on the hair, or used by other similar methods. For example, hair surface modification effects of antioxidation, conditioning, moisturizing, blocking ultraviolet rays, applying a fragrance, a dye, or a powder, bioconjugation, inhibiting bacteria, preventing and improving dandruff, stimulating hair growth, stimulating hair regrowth, and the like may be exhibited, but the present invention is not limited thereto.

The term "fabric care effect" used herein refers to a function of imparting a softening effect to a fabric, preventing damage caused by light; suppressing formation of a wrinkle in a fabric, allowing the formed wrinkle to be easily removed, vivifying the original color of a fabric, maintaining the original feeling of color thereof for a long time, dyeing a fabric, allowing surface contamination to be easily removed, imparting fragrance, removing an odor, repelling bacteria or pests, preventing damage caused by washing, preventing penetration of rain and the like, reinforcing penetration into the inside of a fabric, allowing a fabric to be easily ironed, allowing a fabric to be quickly dried, imparting gloss to a fabric, imparting elasticity to a fabric, preventing a contaminant from being easily adhered to a fabric, preventing static electricity, strengthening a fabric, thickening a fabric, forming a coating on a fabric surface, providing moisture, reinforcing heat insulation and cold insulation, preventing oxidation, blocking ultraviolet rays, stimulating penetration of an active ingredient into a fabric or improving a retention time thereof, reducing the occurrence of fluff, preventing a fabric from being entangled, or enhancing skin friendliness of a fabric.

The term "skin surface-modifying component" used herein may be a component for antioxidation; conditioning (imparting gloss to the skin); moisturizing; whitening; blocking ultraviolet rays; imparting fragrance; preventing or improving a wrinkle; keratin care; preventing or improving dandruff/itching; stimulating hair growth; preventing acne or inhibiting bacteria; suppressing body odor; atopic dermatitis care; pore care; epilation; fingernail and toenail care; or bioconjugation, or a component in the form of a dye or a powder, but the present invention is not limited thereto.

The term "hair surface-modifying component" used herein may be a component for antioxidation, conditioning (enhancing tensile strength, thickness, elasticity, or gloss, moisturizing, preventing damage, repairing damage, preventing the hair from being split, reducing a break in the hair, improving splitting of the hair, nourishing, dyeing, bleaching, styling, decreasing friction, perming, removing chlorine, removing saltiness, preventing static electricity, decreasing porosity, volumizing, hair enrichment, reducing fuzziness, strengthening curls, forming a film and a thin film, softening, eliminating frizz, or enhancing smoothness), moisturizing, blocking ultraviolet rays, applying a fragrance or a dye, bioconjugation, inhibiting bacteria, stimulating hair growth, stimulating hair regrowth, or the like, but the present invention is not limited thereto.

The antioxidation component among the skin-modifying components or the hair-modifying components may be an antioxidation component with an ability to significantly reduce or prevent the destruction and depletion of the function and structure of skin damaged by oxidation, such as extracts derived from natural materials such as animals, plants, minerals, and the like, fermented extracts, amino acids, peptides, proteins, and the like, but the present invention is not limited thereto. For example, the antioxidation component may be one or more selected from the group consisting of acetamido caproic acid, acetyl benzoyloxy prasterone, acetylcysteine, 2-acetylhydroquinone, adamantanylcarboxamido hydroxylbenzamide, aminoethanesulfinic acid, aminopropyl ascorbyl phosphate, angoroside C, anserine, apigenin, arbutin, alpha-arbutin, ascorbic acid, asiaticoside, benzoguanamine, butylhydroxyanisol (BHA), butylated hydroxytoluene (BHT), bis-hydroxyethyl tocopherylsuccinoylamido hydroxypropane, bis-(tetramethyl hydroxypiperidinyl)sebacate), butylated xylenol, t-butylbenzamido hydroxylbenzamide, 4-butylresorcinol, caffeic acid, calcium ascorbate, carnosic acid, carotenoids, chitosan ascorbate, chlorogenic acid, cobalt DNA, copper adenosine triphosphate (ATP), copper pyridoxal 5-phosphate, curcumin, cysteine, cysteine hydrochloride (HCl), decapeptide-6, decapeptide-7, decursinol, decyl mercaptomethylimidazole, diamylhydroquinone, di-t-butylhydroquinone, dicetyl thiodipropionate, dicyclopentadiene/t-butylcresol copolymer, digalloyl trioleate, diisooctyl sebacate, dilauryl thiodipropionate, dimethoxybenzamido phenylhydroxylacetamide, dimethoxy di-p-cresol, dimethylmethoxy chromanol, dimyristyl thiodipropionate, dioleyl tocopheryl methylsilanol, diosmine, diretinyl ether, disodium ascorbyl sulfate, distearyl thiodipropionate, ditridecyl thiodipropionate, dodecyl gallate, *dunaliella* bardawil powder, ellagic acid, epigallocatechin gallate, ergothioneine, *Eriobotrya japonica* leaf protoplasts, erythorbic acid, ethylbisiminomethylguaiacol manganese chloride, ethyl ferulate, ethylhexyl ferulate, ferulic acid, feruloyl soy glycerides, furfuryl palmitate, genistein glucoside, *Ginkgo* leaf terpenoids, glucosylrutin, glyceryl chromonyl ether, glyceryl diferulate, hesperetin, hexyloxy trimethylphenol, honokiol, hydrolyzed proanthocyanidin, hydroquinone, p-hydroxyanisole, hydroxydecyl ubiquinone, hydroxylamine hydrochloride (HCl), hydroxylamine sulfate, hydroxyphenyl dihydroxybenzamide, inositol hexaniacinate hexaascorbate, isooctyl caprylate/caprate, isooctyl thioglycolate, isoquercitrin, kaempferol, kojic acid, kojyl glucoside, kojyl methylenedioxycinnamate, kou-cha ekisu, lycopene, madecassoside, magnesium ascorbate, magnolol, manganese adenosine triphosphate (ATP), matrine, melatonin, methoxy PEG-7 ascorbic acid, methoxytrimethylphenyl dihydroxyphenyl propanol, methyl di-t-butyl hydroxyhydrocinnamate, methylene di-t-butylcresol, methyl methacrylate/trimethoxysilylpropyl methacrylate crosspolymer, methyl myristic acid, niacinamide hydroxybenzoate, nictoflorin, nordihydroguaiaretic acid, octanicotinoyl epigallocatechin gallate, octapeptide-4, oligopeptide-28, paeonol, palmatine, PEG/PPG-2/5 tocopheryl ether, perillyl alcohol, phenethyl caffeate, phenylethyl resorcinol, phenylthioglycolic acid, phloretin, phloroglucinol, piceatannol, piperlonguminine, porphyridium polysaccharide, potassium ascorbyl tocopheryl phosphate, potassium sulfite, PPG-2 tocophereth-5, propyl gallate, protocatechuic aldehyde, puerarin, pyridoxine hydroxybenzoate, pyridyloxide t-butylnitrone, quercetin, resacetophenone, resorcinol, resveratrol, retinyl formyl aspartamate, rosmarinic acid, rutin, rutinyl succinate, ryokucha ekisu, salnacedin, sodium ascorbate, sodium sulfite, sodium tocopheryl phosphate, sodium erythorbate, sodium phosphono-pyridoxylidenerhodanine, sodium thioglycolate, sodium zinc histidine dithiooctanamide, sorbityl furfural, stearyl gallate, succinoyl ascorbate pentapeptide-6, tangeritin, tert-butylhydroquinone (TBHQ), tetrabutyl ethylidinebisphenol, tetrahydrodemethoxydiferuloylmethane, tetrahydrocurcumin diacetate, tetrahydrodiferuloylmethane, tetramethylbutyl dihydroxybenzamide, tetramethylchromanol glucoside, thioctic acid, thiodiglycol, thiolactic acid, thiosalicylic acid, thioaurine, thymol trimethoxycinnamate, tococysteamide, tocophereth-5, tocopherols, tocophersolan, tocopheryl acetate, tocoquinone, toluene, o-tolyl biguanide, totarol, tripropylene glycol, tris-BHT mesitylene, tris(nonylphenyl)phosphite, trisodium ascorbyl isopalmitate phosphate, tyrosyl histidine hydrochloride (HCl), ubiquinol, ubiquinone, *Ulva lactuca* powder, uuron-cha ekisu, xylyl dibutylbenzofuranone, zinc adenosine triphosphate (ATP), zinc dibutyldithiocarbamate, zinc fructose diphosphate, zinc pyridoxal 5-phosphate, and a derivative thereof, but the present invention is not limited thereto.

The conditioning component among the skin-modifying components or the hair-modifying components may be a component for providing a conditioning effect capable of filling a damaged portion of skin or hair, such as extracts derived from natural materials such as animals, plants, minerals, and the like, amino acids, peptides, proteins, and the like, but the present invention is not limited thereto. For example, the component having a conditioning effect may be one or more selected from the group consisting of natural extracts, amino acids, peptides, proteins, polymers, silicones, fatty alcohols, fatty acids, waxes, esters, fatty amidoamines, hydrocarbons, alky glyceryl esters, polyhydric alcohols, sugars, surfactants, powders and dyes, polyethylene, polypropylene, ceramides, vitamins, alkylamines, alkyl amidoamines, and a derivative thereof, but the present invention is not limited thereto.

The natural material-derived extract may be an algae extract, a *Helianthus annuus* seed extract, a *Sophora flavescens* extract, a *Panax ginseng* root extract, a *Coptis chinensis* root extract, a *Calendula officinalis* extract, *Betula platyphylla* sap, a *Betula alba* extract, a *Zanthoxylum bungeanum* maxim extract, a *Luffa cylindrical* extract, a *Monarda didyma* extract, a *Chamaecyparis obtusa* extract, a *Rhodiola rosea* extract, a *Sophora flavescens* extract, an *Atractylodes rhizome* extract, a *Centella asiatica* extract, a *Coptis chinensis* extract, red *ginseng* root water, a *Fritillaria ussuriensis* extract, a *Convallaria keiskei* extract, a cassis extract, a pomegranate extract, a lemon extract, a pine bud extract, a green tea extract, a broccoli extract, a honeycomb extract, a honey extract, propolis, royal jelly, a cranberry extract, a berry extract, a lavender extract, a lentil extract, a ginger extract, or the like. The protein and the peptide may be a protein and a peptide which are obtained from Chunzam silk, silk, polylysine, algae, wool and hair, or wheat, but the present invention is not limited thereto.

The amino acid may be glycine, alanine, valine, leucine, isoleucine, threonine, serine, cysteine, cystine, methionine, aspartic acid, asparagine, glutamic acid, diiodotyrosine, lysine, arginine, histidine, phenylalanine, tyrosine, tryptophan, proline, oxyproline, or the like, but the present invention is not limited thereto.

In addition, the polymer may be a linear/branched chain-type or network-type polymer compound having a molecular weight of about 1,000 to 1,000,000, may include a double bond or various ring-structural substituents between carbon atoms as necessary, and preferably includes at least one residue with reactivity in the molecule to attach a bioreactive group such as —COONa, —COOK, —COOH, —NH$_2$, —NHR, —NR$_2$, —Cl, —Br, —I, or —F for easily attaching a bioreactive functional group to any one terminus of the molecule. More preferably, the polymer is a compound which is a linear/branched chain-type polymer having about 10,000 to 500,000 carbon atoms and includes at least one residue with reactivity in the molecule to attach a bioreactive group such as —COONa, —COOK, —COOH, —NH$_2$, —NHR, —NR$_2$, —Cl, —Br, —I, or —F for easily attaching a bioreactive functional group to any one terminus of the molecule. For example, the polymer may be an amphoteric polymer such as a polyamine polymer, a polycarboxylic acid polymer, a methacryloyl ethyl betaine/methacrylate copolymer, or an octylacrylamide/acrylate/butylaminoethyl methacrylate copolymer, a nonionic polymer such as polyvinylpyrrolidone (PVP), a PVP/vinyl acetate (VA) copolymer, or a PVP/dimethylaminoethyl methacrylate copolymer, or an anionic polymer such as an acrylate/methacrylate copolymer or a VA/crotonate/vinyl neodecanoate copolymer, but the present invention is not limited thereto.

The silicone may be, for example, a compound such as dimethicone, trimethicone, phenyl amodimethicone, amodimethicone, amodi phenyl trimethicone, amodi-penta phenyl trimethicone, dimethylpolysiloxane, methylphenylpolysiloxane, decamethylcyclopentasiloxane, methyl trimethicone, phenyl trimethicone, methicone, cyclomethicone, alkyl methyl siloxane, dimethicone copolyol, or trimethylsilylamodimethicone, but the present invention is not limited thereto.

The fatty alcohol is a C10 to C50 linear/branched fatty alcohol compound, and preferable examples thereof include lauryl alcohol, cetyl alcohol, stearyl alcohol, isostearyl alcohol, behenyl alcohol, and the like, but the present invention is not limited thereto.

The fatty acid is a C10 to C50 linear/branched fatty acid compound, and preferable examples thereof include 18-methyl eicosanoic acid, lauric acid, stearic acid, isostearic acid, and the like, but the present invention is not limited thereto.

The wax may be, for example, candelilla wax, carnauba wax, ricebran wax, beeswax, lanoline, ozokerite, ceresin wax, paraffin wax, microcrystalline wax, polyethylene wax, or the like, but the present invention is not limited thereto.

The ester may be, for example, isopropyl myristate, butyl myristate, isopropyl palmitate, ethyl stearate isopropyl linoleate, decyl myristate, cetyl myristate, cetyl palmitate, hydrogenated polyisobutene, or the like, but the present invention is not limited thereto.

The fatty amidoamine may be, for example, stearyl amidopropyl amine, isostearyl propyl amido amine, stearyl amido amine, isostearyl propyl amido amine, methyleicosanoic amidopropyl amine, methyleicosanoic amidoamine, behenyl amidopropyl amine, behenyl amidoamine, or the like, but the present invention is not limited thereto.

The sugar may be diose- to hexose-monosaccharides such as glycolaldehyde, glyceraldehyde, dihydroacetone, erythrose, erythrulose, ribose, arabinose, xylose, ribulose, xylulose, glucose, fructose, galactose, and mannose; disaccharides such as sucrose, maltose, lactose, trehalose, melibiose, and cellobiose; polysaccharides such as raffinose, melezitose, maltoriose, starchiose, oligosaccharides, galactooligosaccharides, isomaltooligosaccharide, fructooligosaccharides, xylan, araban, starch, dextrins, glycogen, cellulose, fructans, galactan, and mannan; or complex polysaccharides such as agar, algin, carrageenans, chitin, hemicelluloses, and pectin, but the present invention is not limited thereto.

The ceramide is a material with a structure in which a fatty acid is bonded to the amino group of a sphingosine, and the class of ceramides includes natural/synthetic ceramides. For example, the ceramide may be sphingosine, sphinganine, sphingenine, 2-amino-4-eicosane-1,3 diol, ceramides, spingomyelin, cerebrosides, gangliosides, sphingolipids, or derivatives thereof, but the present invention is not limited thereto.

The moisturizing component among the skin-modifying components or the hair-modifying components may be a moisturizing component capable of filling a damaged portion of skin or hair, such as extracts derived from natural materials such as animals, plants, minerals, and the like, amino acids, peptides, proteins, sugars, vitamins, and the like, but the present invention is not limited thereto. For example, the moisturizing component may be one or more selected from the group consisting of PPG-arginine, glycerin, propylene glycol, butylene glycol, dipropylene glycol, caprylyl glycol, diglycerin, methyl gluceth, ethoxydiglycol, glycereth, propanediol, diethoxydiglycol pyrrolidone carboxylic acid, sodium lactate, sodium PCA, mineral oil, vaseline, lanolin, jojoba oil, olive oil, glycosphingolipids, phospholipids, lipid composites, isononyl isononanoate, betaines, carboxymethyl chitin, ceramides, glucosylceramide, glycosaminoglycans, alpha-glucans, hyaluronic acid, hydrolyzed hyaluronic acid, betaines, chitosan, chitosan succinamide, vitamin E (tocopherols), urea, hydroxyethyl urea, glucosides, gamma PGA, xylitylglucoside, xylitol, pentaerythrityl tetraisostearate, sodium chondroitin sulfate, chondroitin-4-sulfate, atelocollagen, beta-glucan, PEG, pyridoxine tris-hexyl decanoate, potassium PCA, sodium polygamma-glutamate, polyglutamic acid, glyceryl polyacrylate, galactoarabinan, polyglycerin-3 crosspolymer, sodium hyaluronate, bis-PEG-18 methyl ether dimethyl silane, bis-ethoxydiglycol succinate, lecithin, ascorbyl tetraisopalmitate, glycosyl trehalose, hydrogenated starch hydrolysate, 1,2-hexanediol, mannitol, arginine, serine, sucrose, PCA, citrulline, glycogen, histidine HCl, alanine, threonine, glutamic acid, lysine HCl, phosphate buffered saline, creatine, cholesteryl isostearate, cholesteryl chloride, cholesteryl nonanoate, butylhydroxytoluene (BHT), sodium dilauramidoglutamide lysine, maltodextrin, polyquaternium-39, cholecalciferol PEG-12 ether, saccharide isomerate, sorbitol, and derivatives thereof, but the present invention is not limited thereto.

The whitening component among the skin-modifying components may be a whitening component capable of improving the conditions of an area damaged by melanin pigmentation, such as extracts derived from natural materials such as animals, plants, minerals, and the like, amino acids, hormones, vitamins, and the like, but the present invention is not limited thereto. For example, the whitening component may be one or more selected from the group consisting of kojic acid, niacinamide, ascorbyl glucoside, magnesium ascorbyl phosphate, acetyl tyrosine, fullerene, oryzanol, methoxy PEG-7 ascorbic acid, methyl undecenoyl leucinate, diacetyl benzoyllathyrol, protocatechuic aldehyde, alpha-bisabolol, dihydroxymethoxychalcone, acetylphytosphingosine, polydatin, diosmetin, azelaic acid, macelignan, a *Panax ginseng* root extract, a red *ginseng* root extract, a scrophularia root extract, a lithospermum root extract, a *Saururus chinensis* extract, an agrimony extract, a *Canna indica*'s root extract, a *Sasa quelpaertensis* extract, a *Sophora flavescens* extract, a *coix* seed extract, an *Atracty-*

*lodis rhizoma* alba extract, a wheat germ extract, an *Atractylodis rhizoma* alba oil, and a *Prunus domestica* fruit extract.

The component for blocking ultraviolet rays among the skin-modifying components or the hair-modifying components may be an ultraviolet ray absorbent such as a p-aminobenzoic acid derivative, a cinnamic acid derivative, a salicylic acid derivative, a benzophenone derivative, or the like, an ultraviolet ray dispersing agent such as titanium oxide, zinc oxide, or the like, a resin such as a cellulose-based polymer, a PVP/alpha-olefin-based polymer, an acrylate polymer, a silicone resin, a fluorine-modified silicone resin, or the like, or a polymer film-forming agent. A component having a substantial function of blocking ultraviolet rays may be, for example, one or more selected from the group consisting of cinnamic acid, glyceryl PABA, drometrizole, digalloyl trioleate, 3-(4-methylbenzylidene) camphor, menthyl anthranilate, benzophenone-3, benzophenone-4, benzophenone-8, butylmethoxy benzoylmethane, cinoxate, adenine riboside, octocrylene, octyl dimethyl PABA, octyl methoxycinnamate, octyl salicylate, octyl triazone, para-aminobenzoic acid, 2-benzimidazole-5-sulfonic acid, homosalate, zinc oxide, titanium dioxide, isoamyl-p-methoxycinnamate, bis-ethylhexyloxyphenol methoxyphenyltriazine, disodium phenyl dibenzimidazole tetrasulfonate, amodi-drometrizole trisiloxane, diethylhexyl butamido triazone, polysilicon-15 (dimethicodiethylbenzalmalonate), methylene bis-benzotriazolyl tetramethylbutylphenol, terephthalylidene dicamphor sulfonic acid, and a salt thereof, but the present invention is not limited thereto.

The fragrance component among the skin-modifying components or the hair-modifying components may be, for example, aldehydes, phenols, alcohols, ethers, esters, hydrocarbons, ketones, lactones, musks, fragrances with a terpene skeleton, natural fragrances, animal fragrances, or the like. Non-limiting examples of the aldehydes include undecylenic aldehyde, lauryl aldehyde, aldehyde C-12 MNA, myrac aldehyde, α-amyl cinnamic aldehyde, cyclamen aldehyde, ethylvanillin, heliotropin, anisaldehyde, α-hexyl cinnamic aldehyde, octanal, ligustral, lilial, lyral, triplal, vanillin, helional, or the like. Non-limiting examples of the phenols include eugenol, isoeugenol, and the like. Non-limiting examples of the alcohols include bacdanol, dihydromyrcenol, dihydrolinalool, linalool, nerol, santalol, santalex, terpineol, tetrahydrolinalool, phenylethyl alcohol, and the like. Non-limiting examples of the ethers include Cedramber, Grisalva, methyleugenol, methyl isoeugenol, and the like. Non-limiting examples of the esters include cis-3-hexenyl acetate, cis-3-hexenyl propionate, cis-3-hexenyl salicylate, p-cresyl acetate, p-tert-butylcyclohexyl acetate, amyl acetate, methyl dihydrojasmonate, amyl salicylate, benzyl salicylate, benzyl benzoate, benzyl acetate, cedryl acetate, citronellyl acetate, decahydro-β-naphthyl acetate, dimethyl benzyl carbinyl acetate, Erica propionate, ethyl acetoacetate, Erica acetate, geranyl acetate, geranyl formate, hedione, linalyl acetate, β-phenylethyl acetate, hexyl salicylate, styrallyl acetate, terpinyl acetate, vetiveryl acetate, o-tert-butylcyclohexyl acetate, manzanate, allyl heptanoate, cinnamyl acetate, and the like. Non-limiting examples of the hydrocarbons include myrcene or the like. Non-limiting examples of the ketones include α-ionone, β-ionone, methyl-β-naphthyl ketone, α-damascone, β-damascone, δ-damascone, cis-jasmone, methyl ionone, allyl ionone, cashmeran, dihydrojasmone, iso E Super, vertofix, isolongifolanone, Koavone, rose phenone, raspberry ketone, dynascone, and the like. Non-limiting examples of the lactones include γ-decalactone, γ-undecalactone, γ-nonalactone, γ-dodecalactone, coumarin, ambroxan, and the like. Non-limiting examples of the musks may include cyclopentadecanolide, ethylene brassylate, galaxolide, musk ketone, tonalid, nitro musk, and the like. Non-limiting examples of the fragrances with a terpene skeleton include geraniol, nerol, linalool, citral, citronellol, menthol, mint, citronellal, myrcene, pinene, limonene, terpineol, carbone, ionone, camphor, borneol, and the like. Non-limiting examples of the natural fragrances include essential oils such as orange oil, lemon oil, lime oil, petitgrain oil, yuja oil, neroli oil, bergamot oil, lavender oil, lavandin oil, *abies* oil, anise oil, bay oil, rosewood oil, ylang-ylang oil, citronella oil, geranium oil, peppermint oil, menthol oil, spearmint oil, *eucalyptus* oil, lemon grass oil, patchouli oil, jasmine oil, rose oil, cedarwood oil, vetiver oil, *galbanum* oil, oakmoss oil, pine oil, camphor oil, sandalwood oil, hosho oil, turpentine oil, clove oil, black clove oil, *cassia* oil, netmeg oil, *cananga* oil, thyme oil, and the like. Non-limiting examples of the animal fragrances include musk, citvet, castoreum, ambergris, and the like.

The component for preventing or improving a wrinkle among the skin-modifying components may include extracts derived from natural materials such as animals, plants, minerals, and the like, amino acids, hormones, vitamins, and the like, but the present invention is not limited thereto. For example, the component for preventing or improving a wrinkle may be one or more selected from the group consisting of vitamin A (retinoids), vitamin E (tocopherols), flavonoids, polyphenols, superoxide dismutase (SOD), coenzyme Q10, alpha-lipoic acid, acetyl hexapeptide, retinol, retinyl palmitate, retinyl acetate, adenosine, vitamin C, collagen, hexapeptide-3, epidermal growth factor (EGF), kinetin, snail slime, aquamide, ceramides, glycerine, hyaluronic acid, betaines, chitosan, urea, and derivatives thereof, but the present invention is not limited thereto.

The keratin care component among the skin-modifying components may be an alpha hydroxyl acid (lactic acid, citric acid, mandelic acid, glycolic acid, tartaric acid, or the like), a beta hydroxy acid (salicylic acid, propanoic acid, hydroxypropionic acid, carnitine), a retinoid derivative, a vitamin A derivative, a Rhynchosia nulubilis extract, black soybean powder, a sugarcane extract, rice bran powder, *Astrocaryum murumuru* seed powder, nephrite powder, a hydrolyzed *Cereus* grandiorus flower extract, thioglycolic acid, or the like, but the present invention is not limited thereto.

The component for preventing or improving dandruff and itching among the skin-modifying components may include extracts derived from natural materials such as animals, plants, minerals, and the like, amino acids, hormones, vitamins, and the like, but the present invention is not limited thereto. For example, the component for preventing or improving dandruff and itching may be one or more selected from the group consisting of a moisturizing component such as ceramides, glycerine, hyaluronic acid, betaines, chitosan, vitamin E (tocopherols), and urea; a pharmaceutical hair growth agent including a vasodilator, a hair tonic, estrogen hormone, a hair root activating agent, and the like; an anti-inflammatory agent and a keratolytic agent such as d-panthenol, sulfur, resorcin, serine chloride, allantoin, AHA, salicylic acid, or the like; an agent for preventing skin damage such as an astringent, a refrigerant, vitamin, hormone, antihistamine, or the like; a sebum secretion inhibitor; an antibacterial agent such as trichlorocarbamide, tocopherol acetate, zinc pyrithione, benzalkonium chloride, benzethonium chloride, chlorhexidine, hinokitiol, phenol, isopropyl methylphenol, or the like; an antiseborrheic agent such as pyridoxine and a derivative thereof, or the like; an anti-inflammatory agent such as glychyrrhetinic acid and a derivative thereof, hydrocortisone acetate, hydrocortisone succinate, prednisolone, or the like; an antipruritic agent such as diphenhydramine chloride, chlorophenylamine maleate, camphor, menthol, or the like; and other agents such as alanine glutamine, bisabolol, allantoin, coenzyme Q10, stearyl glycyrrhetinate (SG)/dipotassium glycyrrhizinate (DPG), phytosphingosine and a derivative thereof.

The component for stimulating hair growth or stimulating hair regrowth among the skin-modifying components or the hair-modifying components may be a component for stimulating hair growth capable of filling a damaged portion of skin or hair, such as extracts derived from natural materials such as animals, plants, minerals, and the like, amino acids, peptides, proteins, sugars, vitamins, and the like, but the present invention is not limited thereto. For example, the component for stimulating hair growth may be one or more selected from the group consisting of a *Swertia japonica* extract, carpronium chloride, cepharanthin, benzyl nicotinate, 1-menthol, estradiol, etynlyestradiol, pyridoxine HCl, salicylic acid, resorcin, benzalkonium chloride, benzethonium chloride, isopropyl methylphenol, piroctone olamine, climbazole, pantothenic acid, a placenta extract, biotin, mononitroguajacol, a photosensitizing dye, pentadecanoic acid glyceride, glycyrrhetinic acid, a potassium or ammonium salt of glycyrrhetinic acid, allantoin, minoxidil, steroids, estradiol benzoate, estrone, hydrocortisone (acetate), prednisolone, diphenhydramine HCl, dipotassium glycyrrhizinate, pyridoxine dicaprylate, tricosaccharide, tocopherol/tocopherol acetate, hinokitiol, dexpanthenol, pantothenyl ethylether, sodium/calcium pantothenate, isopropyl ethylphenol, mononitroguajacol, chlorhexidine gluconate solution, ethyl nicotinate, nicotinic acid amide, *capsicum* tincture, reisogen, cholesterol, swertiol, fused cystine, *Sophora flavescens* tincture, *Asarum* tincture, a *Spirodela polyrhiza* extract, a *Swertia pseudochinensis* extract, cepharanthin, gamma-oryzanol, cantharis tincture, ginger tincture, nicotinic acid benzyl ester, vitamin A, vitamin B1, vitamin B2, vitamin B6, vitamin E, cystine, cysteine, methionine, leucine, tryptophan, glycerine, pyrrolidone carboxylate, and camphor.

The component for preventing acne or inhibiting bacteria among the skin-modifying components may be a component for preventing acne or inhibiting bacteria capable of improving an area damaged by melanin pigmentation, such as extracts derived from natural materials such as animals, plants, minerals, and the like, amino acids, hormones, vitamins, and the like, but the present invention is not limited thereto. For example, the component for preventing acne or inhibiting bacteria may be one or more selected from the group consisting of a sebum secretion inhibitor such as estradiol, estrone, or ethynylestradiol; a keratolytic agent such as sulfur, salicylic acid, or resorcin; an antibacterial agent such as benzalkonium chloride, benzethonium chloride, halocarbon, or 2,4,4-trichloro-2-hydroxyphenol; an antibacterial agent for cosmetics, such as triclosan, trichloro carbitol, isopropyl methylphenol, or pinyon; an anti-inflammatory agent such as allantoin, ε-aminocaproic acid, or glychyrrhetinic acid; and a keratolytic agent such as glycolic acid or the like.

The component for suppressing body odor among the skin-modifying components may be, for example, one or more selected from the group consisting of aluminum compounds such as aluminum chlorohydroxy, aluminum chlorohydroxy allantoinate, aluminum dihydroxy allantoinate, aluminum chloride, and aluminum potassium sulfate, benzethonium chloride, halocarane, chlorhexidine hydrochloride, zinc oxide, zinc p-phenolsulfonate, benzalkonium chloride, triclosan, thiram, a Psolarea coryifolia extract, a *Pueraria lobata* root extract, a *Ionicera japonica* flower extract, a Phyllostachyos caulis extract, an Acorus calamus extract, a *Ginkgo biloba* leaf extract, a Moutan radices cortex extract, a licorice extract, a Fallopian *multiflora* extract, a *Houttuynia cordata* extract, a *Portulaca oleracea* extract, pyroligneous liquor, bamboo salt, a grapefruit extract, a green tea extract, and a *Paeonia lactiflora* extract.

The component for atopic dermatitis care among the skin-modifying components may be a component for atopic dermatitis or skin trouble care with an ability to significantly reduce or prevent atopic dermatitis or skin trouble due to having functions such as skin soothing, regeneration, immunity improvement, and the like, such as drugs derived from natural materials such as animals, plants, minerals, and the like, fermented extracts, herbal ingredients, vitamins, and the like, but the present invention is not limited thereto. For example, the component for atopic dermatitis care may be one or more selected from the group consisting of ceramides, peptides, hyaluronic acid, glycerine, tacrolimus, pimecrolimus, clindamycin, erythromycin, tretinoin, adapalene, benzoyl peroxide, licorice, epidermal growth factor (EGF), peanut oil, Macadamia *Ternifolia* seed oil, propolis, an olive leaf extract, a Siberian *ginseng* extract, a *Houttuynia cordata* extract, an *arnica* extract, and *Sophora flavescens* tincture. The peptides may be, specifically, wheat peptides, wheat-hydrolyzed peptides, keratin peptides, keratin-hydrolyzed peptides, collagen peptides, collagen-hydrolyzed peptides, or the like, but the present invention is not limited thereto.

The component for pore care among the skin-modifying components may be niacinamide, polyethoxylated retinamide, adenosine, menthol, a witch-hazel extract, ascorbic acid, kaolin, retinol, a *Vitis vinifera* root extract, clays, asiaticoside, a Cynara scolymus leaf extract, glycosyl trehalose, hydrogenated starch hydrolysate, lecithin, tocopherols, charcoal powder, or the like, but the present invention is not limited thereto.

The epilation component among the skin-modifying components may be thioglycolic acid, beeswax, a *Narcissus tazetta* bulb extract, a *papaya* extract, a *Quercus dentata* extract, or the like, but the present invention is not limited thereto.

The dye among the skin-modifying components or the hair-modifying components may include one or more atomic groups selected from the group consisting of $-NO_2$, $-N=N-$, $C=O$, $C=C$, $C=N-$, $C=S$, $-N=O$, and $-N=NO$ as a chromophore, but the present invention is not limited thereto. Also, the dye may include one or more atomic groups selected from the group consisting of $-OCH_3$, $-N(CH_3)_2$, $-NH(CH_3)$, $-NO_2$, $-CF_3$, $-OH$, $-OCH_3$, $-Cl$, and $-NH_2$ as an auxochrome, but the present invention is not limited thereto. In addition, the dye may include one or more reactive groups selected from the group consisting of $-COONa$, $-COOK$, $-COOH$, $-NH_2$, $-NHR$, $-NR_2$, $-Cl$, $-Br$, $-I$, and $-F$, but the present invention is not limited thereto. Additionally, the dye may be a natural or synthetic dye used for hair, skin, fingernails and toenails, and the like. In this case, the natural dye may be purpurin, munjistin, melanin, or a melanin precursor, but the present invention is not limited thereto. The synthetic dye may be Red No. 3, Red No. 104, Red No. 105, Red No. 201, Red No. 202, Red No. 220, Red No. 227, Black No. 401, Red No. 230, Red No. 231, Red No. 232, Red No. 401, Red No. 405, Yellow No. 4, Yellow No. 202, Orange No. 207, Red No. 106, Red No. 213, Red No. 214, Red No. 215, Yellow No. 404, Yellow No. 405, Blue No. 403, Disperse Blue 1, Disperse Violet 1, Disperse Orange 3, Disperse Black 9, HC Blue 2, HC Red 3, HC Yellow 5, HC Red 1, Basic Orange 1, or Basic Orange 2, but the present invention is not limited thereto.

The powder among the skin-modifying components may be titanium dioxide, hydroxyapatite, triethoxycaprylylsilane, aluminum hydroxide, zinc oxide, talc, mica, a yellow iron oxide, a red iron oxide, a black iron oxide, silica, an acrylate copolymer, guanine, guaiazulene, copper powder, aluminum stearate, orthoclase, zinc stearate, bronze powder, *gardenia* blue pigment, a *Gardenia* extract, *gardenia* yellow pigment, caramel, carmine, carbon, carbon black, copper chlorophyll, a henna leaf extract, a henna extract, *Vitis vinifera* powder, a *Vitis vinfera* skin extract, a wine extract, a *Vitis vinifera* extract, loess, or the like, but the present invention is not limited thereto.

The component for fingernail and toenail care among the skin-modifying components may be a *Viscum album* extract, a *Commelina communis* leaf/flower/stem extract, dimethyltolylamine, methacryloyl ethyl phosphate, a *Commiphora abyssinica* resin extract, butyl methacrylate, AMP-isostearoyl hydrolyzed silk, an *Echinacea* root extract, a *Lycium barbarum* fruit extract, urea peroxide, calcium peroxide, keratin, potassium hydroxide, hydrogen peroxide, hydrolyzed keratin, hydrolyzed collagen, or the like, but the present invention is not limited thereto.

The bioconjugation component among the skin-modifying components or the hair-modifying components may be fibrin, albumin, glucosamine, n-acetylglucosamine, alginate, hydrogel, growth factors, bioactive factors, a split hair bonding agent, an antibacterial coating agent, or the like. The growth factors may be, for example, fibroblast growth factors (FGFs), keratinocyte growth factors (KGFs), vascular endothelial growth factors (VEGFs), epidermal growth factors (EGFs), platelet derived growth factor AA (PDGF-AA), platelet derived growth factor AB (PDGF-AB), platelet derived growth factor BB (PDGF-BB), transforming growth factor-α (TGF-α), TGF-β, insulin-like growth factors (IGFs), tumor necrosis factors (TNFs), granulocyte macrophage colony stimulating factors (GM-CSFs), nerve growth factors (NGFs), or the like. The bioactive factors may be interferons, hemopoietin, IL-1 (interleukin-1), IL-2, IL-6, IL-8, or the like. The split hair bonding agent may be N-(4-carboxy-3-hydroxy-phenyl)maleimide, transglutaminase, lauryl diamine, or the like. The antibacterial coating agent may be benzalkonium chloride, benzethonium chloride, halocarbon, 2,4,4-trichloro-2-hydroxyphenol, triclosan, trichloro carbitol, isopropyl methylphenol, pinyon, allantoin, s-aminocaproic acid, glychyrrhetinic acid, or the like, but the present invention is not limited thereto.

The antibacterial component among the hair surface-modifying components may be ceramides, glycerine, hyaluronic acid, betaines, chitosan, vitamin E (tocopherols), urea, d-panthenol, sulfur, resorcin, serine chloride, allantoin, AHA, salicylic acid, trichlorocarbamide, tocopherol acetate, zinc pyrithione, benzalkonium chloride, benzethonium chloride, chlorhexidine, hinokitiol, phenol, isopropyl methylphenol, phenoxyethanol, isothiazolinone, methylchloroisothiazolinone, pyridoxine, glychyrrhetinic acid, hydrocortisone acetate, hydrocortisone succinate, prednisolone, diphenhydramine chloride, chlorophenylamine maleate, camphor, menthol, alanine glutamine, bisbolol, coenzyme Q10, stearyl glycyrrhetinate (SG)/dipotassium glycyrrhizinate (DPG), phytosphingosine, or a derivative thereof, but the present invention is not limited thereto.

The term "fabric care component" used herein may be a component for softening a fabric, preventing damage caused by light, inhibiting or removing a wrinkle, maintaining color, dyeing, removing contamination, imparting fragrance, removing an odor, inhibiting bacteria, preventing damage caused by washing, waterproofing, coating, preventing static electricity, moisturizing, heat insulation or cold insulation, antioxidation, blocking ultraviolet rays, preventing fluff from being entangled, or the like, but the present invention is not limited thereto.

The component for softening a fabric, preventing damage, waterproofing, coating, preventing static electricity, and preventing fluff from being formed and entangled may be, for example, dimethicone, trimethicone, phenyl trimethicone, amodimethicone, amodi phenyl trimethicone, amodipenta phenyl trimethicone, dimethylpolysiloxane, methylphenylpolysiloxane, decamethylcyclopentasiloxane, methyl trimethicone, phenyl trimethicone, methicone, cycloniethicone, alkyl methyl siloxane, dimethicone copolyol, trimethylsilylamodimethicone, a fluorine-based silicone compound, or the like, but the present invention is not limited thereto.

In addition, the ceramide, which is effective in softening a fabric and preventing damage, is a material with a structure in which a fatty acid is bonded to the amino group of a sphingosine, and the class of ceramides include natural/synthetic ceramides. For example, the ceramide may be sphingosine, sphinganine, sphingenine, 2-amino-4-eicosane-1,3 diol, ceramides, spingomyelin, cerebrosides, gangliosides, sphingolipids, or a derivative thereof, but the present invention is not limited thereto.

The extract derived from a natural material used to increase the skin friendliness of a fabric may be an algae extract, a *Helianthus annuus* seed extract, a *Sophora flavescens* extract, a *Panax ginseng* root extract, a *Coptis chinensis* root extract, a *Calendula officinalis* extract, *Betula platyphylla* sap, a *Betula alba* extract, a *Zanthoxylum bungeanum* maxim extract, a *Luffa cylindrical* extract, a *Monarda didyma* extract, a *Chamaecyparis obtusa* extract, a *Rhodiola rosea* extract, a *Sophora flavescens* extract, an *Atractylodes rhizome* extract, a *Centella asiatica* extract, a *Coptis chinensis* extract, red *ginseng* root water, a *Fritillaria ussuriensis* extract, a *Convallaria keiskei* extract, a honeycomb extract, a cassis extract, a pomegranate extract, a lemon extract, a pine bud extract, a green tea extract, a broccoli extract, a honey extract, a cranberry extract, a berry extract, a lavender extract, a lentil extract, a ginger extract, or the like. The protein and the peptide may be a protein and a peptide which are obtained from Chun-zam silk, silk, polylysine, algae, wool and hair, or wheat. The amino acid may be glycine, alanine, valine, leucine, isoleucine, threonine, serine, cysteine, cystine, methionine, aspartic acid, asparagine, glutamic acid, diiodotyrosine, lysine, arginine, histidine, phenylalanine, tyrosine, tryptophan, proline, oxyproline, or the like, but the present invention is not limited thereto.

The polymer used to form a coating on a fabric surface, improve prevention of a wrinkle, prevent dye migration, remove fluff during washing, impart elasticity to a fabric, and impart ease of ironing to the fabric may be a linear/branched chain-type or network-type polymer compound having a molecular weight of about 1,000 to 1,000,000, may include a double bond or various ring-structural substituents between carbon atoms as necessary, and preferably includes at least one residue with reactivity in the molecule to attach a bioreactive group such as —COONa, —COOK, —COOH, —NH$_2$, —NHR, —NR$_2$, —Cl, —Br, —I, or —F for easily attaching a bioreactive functional group to any one terminus of the molecule. More preferably, the polymer is a compound which is a linear/branched chain-type polymer having about 10,000 to 500,000 carbon atoms and includes at least one residue with reactivity in the molecule to attach a bioreactive group such as —COONa, —COOK, —COOH, —NH$_2$, —NHR, —NR$_2$, —Cl, —Br, —I, or —F for easily attaching a bioreactive functional group to any one terminus of the molecule. For example, the polymer may be a synthetic polymer such as an amphoteric polymer such as a polyamine polymer, a polycarboxylic acid polymer, a methacryloyl ethyl betaine/methacrylate copolymer, or an octylacrylamide/acrylate/butylaminoethyl methacrylate copolymer; a nonionic polymer such as polyvinylpyrrolidone (PVP), a PVP/vinyl acetate (VA) copolymer, or a PVP/dimethylaminoethyl methacrylate copolymer; or an anionic polymer such as an acrylate/methacrylate copolymer or a VA/crotonate/vinyl neodecanoate copolymer, or a natural polymer derived from cellulose, guar, starch, or the like, but the present invention is not limited thereto.

The dye, which serves to impart color to a fabric and maintain the same, may include one or more atomic groups selected from the group consisting of —NO$_2$, —N=N—, C=O, C=C, C=N—, C=S, —N=O, and —N=NO as a chromophore, but the present invention is not limited thereto. Also, the dye may include one or more atomic groups selected from the group consisting of —OCH$_3$, —N(CH$_3$)$_2$, —NH(CH$_3$), —NO$_2$, —CF$_3$, —OH, —OCH$_3$, —Cl, and —NH$_2$ as an auxochrome, but the present invention is not limited thereto. In addition, the dye may include one or more reactive groups selected from the group consisting of —COONa, —COOK, —COOH, —NH$_2$, —NHR, —NR$_2$, —Cl, —Br, —I, and —F, but the present invention is not limited thereto. Additionally, the dye may be a natural or synthetic dye used for hair, skin, a fabric, leather, and the like. In this case, the natural dye may be purpurin, munjistin, melanin, or a melanin precursor, but the present invention is not limited thereto, and the synthetic dye may be Red No. 3, Red No. 104, Red No. 105, Red No. 201, Red No. 202, Red No. 220, Red No. 227, Black No. 401, Red No. 230, Red No. 231, Red No. 232, Red No. 401, Red No. 405, Yellow No. 4, Yellow No. 202, Orange No. 207, Red No. 106, Red No. 213, Red No. 214, Red No. 215, Yellow No. 404, Yellow No. 405, Blue No. 403, Disperse Blue 1, Disperse Violet 1, Disperse Orange 3, Disperse Black 9, HC Blue 2, HC Red 3, HC Yellow 5, HC Red 1, Basic Orange 1, or Basic Orange 2, but the present invention is not limited thereto.

Examples of the component for removing contamination may include soaps, alkylbenzene sulfonates, alkane sulfonates, alpha-olefin sulfonates, alpha-sulfo fatty acid esters, alkyl sulfates, alkyl ether sulfates, alcohol ethoxylates, alkylphenol ethoxylates, fatty acid alkanolamides, alkylamine oxides, methylglucamides, alkyl polyglucosides, or the like, but the present invention is not limited thereto.

Examples of the component for imparting fragrance may include aldehydes, phenols, alcohols, ethers, esters, hydrocarbons, ketones, lactones, musks, fragrances with a terpene skeleton, natural fragrances, animal fragrances, and the like. Non-limiting examples of the aldehydes include undecylenic aldehyde, lauryl aldehyde, aldehyde C-12 MNA, myrac aldehyde, α-amyl cinnamic aldehyde, cyclamen aldehyde, ethylvanillin, heliotropin, anisaldehyde, α-hexyl cinnamic aldehyde, octanal, ligustral, lilial, lyral, triplal, vanillin, helional, and the like. Non-limiting examples of the phenols include eugenol, isoeugenol, or the like. Non-limiting examples of the alcohols include bacdanol, dihydromyrcenol, dihydrolinalool, linalool, nerol, santalol, santalex, terpineol, tetrahydrolinalool, phenylethyl alcohol, and the like. Non-limiting examples of the ethers include Cedramber, Grisalva, methyleugenol, methyl isoeugenol, and the like. Non-limiting examples of the esters include cis-3-hexenyl acetate, cis-3-hexenyl propionate, cis-3-hexenyl salicylate, p-cresyl acetate, p-tert-butylcyclohexyl acetate, amyl acetate, methyl dihydrojasmonate, amyl salicylate, benzyl salicylate, benzyl benzoate, benzyl acetate, cedryl acetate, citronellyl acetate, decahydro-β-naphthyl acetate, dimethyl benzyl carbinyl acetate, Erica propionate, ethyl acetoacetate, Erica acetate, geranyl acetate, geranyl formate, hedione, linalyl acetate, β-phenylethyl acetate, hexyl salicylate, styrallyl acetate, terpinyl acetate, vetiveryl acetate, o-tert-butylcyclohexyl acetate, manzanate, allyl heptanoate, cinnamyl acetate, and the like. Non-limiting examples of the hydrocarbons include myrcene and the like. Non-limiting examples of the ketones include α-ionone, β-ionone, methyl-β-naphthyl ketone, α-damascone, β-damascone, δ-damascone, cis-jasmone, methyl ionone, allyl ionone, cashmeran, dihydrojasmone, Iso E Super, vertofix, isolongifolanone, Koavone, rose phenone, raspberry ketone, dynascone, and the like. Non-limiting examples of the lactones include γ-decalactone, γ-undecalactone, γ-nonalactone, γ-dodecalactone, coumarin, ambroxan, and the like. Non-limiting examples of the musks include cyclopentadecanolide, ethylene brassylate, galaxolide, musk ketone, tonalid, nitro musk, and the like. Non-limiting examples of the fragrance with a terpene skeleton include geraniol, nerol, linalool, citral, citronellol, menthol, mint, citronellal, myrcene, pinene, limonene, terpineol, carbone, ionone, camphor, borneol, and the like. Non-limiting examples of the natural fragrance include an essential oil such as orange oil, lemon oil, lime oil, petitgrain oil, yuja oil, neroli oil, bergamot oil, lavender oil, lavandin oil, *abies* oil, anise oil, bay oil, rosewood oil, ylang-ylang oil, citronella oil, geranium oil, peppermint oil, spearmint oil, *eucalyptus* oil, lemon grass oil, patchouli oil, jasmine oil, rose oil, cedarwood oil, vetiver oil, *galbanum* oil, oakmoss oil, pine oil, camphor oil, sandalwood oil, hosho oil, turpentine oil, clove oil, black clove oil, *cassia* oil, netmeg oil, *cananga* oil, thyme oil, and the like. Non-limiting examples of the animal fragrance include musk, citvet, castoreum, ambergris, and the like.

The component for removing an odor may be mono-6-ethanediamine-6-deoxy-β-cyclodextrin, α-cyclodextrin, β-cyclodextrin, α-cyclodextrin, cucurbituril, or the like, but the present invention is not limited thereto.

The antibacterial component may be a ceramide, glycerine, hyaluronic acid, betaines, chitosan, vitamin E (tocopherols), urea, d-panthenol, sulfur, resorcin, serin chloride, allantoin, AHA, salicylic acid, trichlorocarbamide, tocopherol acetate, zinc pyrithione, benzalkonium chloride, benzethonium chloride, chlorhexidine, hinokitiol, phenol, isopropyl methylphenol, phenoxyethanol, isothiazolinone, methylchloroisothiazolinone, pyridoxine, glychyrrhetinic acid, hydrocortisone acetate, hydrocortisone succinate, prednisolone, diphenhydramine chloride, chlorophenylamine maleate, camphor, menthol, alanine glutamine, bisabolol, coenzyme Q10, stearyl glycyrrhetinate (SG)/dipotassium glycyrrhizinate (DPG), phytosphingosine, or a derivative thereof, but the present invention is not limited thereto.

The component for preventing static electricity may be stearyl amidopropyl amine, isostearyl propyl amido amine, stearyl amido amine, isostearyl propyl amido amine, methyleicosanoic amidopropyl amine, methyleicosanoic amidoamine, behenyl amidopropyl amine, behenyl amidoamine, or the like, but the present invention is not limited thereto.

The moisturizing component which has effects of moisturizing a fabric, preventing and repairing a wrinkle, preventing static electricity, softening, and heat insulation or cold insulation induced by the action of the fabric with water may be a moisturizing component capable of filling a damaged portion of the fabric, such as extracts derived from natural materials such as animals, plants, minerals, and the like, amino acids, peptides, proteins, sugars, vitamins, and the like, but the present invention is not limited thereto. For example, the moisturizing component may be one or more selected from the group consisting of glycerin, propylene glycol, butylene glycol, dipropylene glycol, caprylyl glycol, diglycerin, methyl gluceth, ethoxydiglycol, glycereth, propanediol, diethoxydiglycol pyrrolidone carboxylic acid, sodium lactate, sodium PCA, mineral oil, vaseline, lanolin, jojoba oil, olive oil, glycosphingolipids, phospholipids, lipid composites, isononyl isononanoate, betaines, carboxymethyl chitin, ceramides, glucosylceramide, glycosaminoglycans, alpha-glucans, hyaluronic acid, hydrolyzed hyaluronic acid, betaines, chitosan, chitosan succinamide, vitamin E (tocopherols), urea, hydroxyethyl urea, glucosides, gamma PGA, xylitylglucoside, xylitol, pentaerythrityl tetraisostearate, sodium chondroitin sulfate, chondroitin-4-sulfate, atelocollagen, beta-glucan, PEG, pyridoxine tris-hexyl decanoate, potassium PCA, sodium polygamma-glutamate, polyglutamic acid, glyceryl polyacrylate, galactoarabinan, polyglycerin-3 crosspolymer, sodium hyaluronate, bis-PEG-18 methyl ether dimethyl silane, bis-ethoxydiglycol succinate, lecithin, ascorbyl tetraisopalmitate, glycosyl trehalose, hydrogenated starch hydrolysate, 1,2-hexanediol, mannitol, arginine, serine, sucrose, PCA, citrulline, glycogen, histidine HCl, alanine, threonine, glutamic acid, lysine HCl, phosphate buffered saline, creatine, cholesteryl isostearate, cholesteryl chloride, cholesteryl nonanoate, BHT, sodium dilauramidoglutamide lysine, maltodextrin, polyquaternium-39, cholecalciferol PEG-12 ether, saccharide isomerate, sorbitol, and a derivative thereof, but the present invention is not limited thereto.

The sugars which has effects of moisturizing a fabric, preventing and repairing a wrinkle, preventing static electricity, softening, and heat insulation or cold insulation induced by the action of the fabric with water may be dioseto hexose-monosaccharides such as glycolaldehyde, glyceraldehyde, dihydroacetone, erythrose, erythrulose, ribose, arabinose, xylose, ribulose, xylulose, glucose, fructose, galactose, and mannose; disaccharides such as sucrose, maltose, lactose, trehalose, and melibiose, cellobise; polysaccharides such as raffinose, melezitose, maltoriose, starchiose, oligosaccharides, galactooligosaccharides, isomaltooligosaccharide, fructooligosaccharides, xylan, araban, starch, dextrins, glycogen, cellulose, fructans, galactan, and mannan; or complex polysaccharides such as agar, algin, carrageenans, chitin, hemicelluloses, and pectin, but the present invention is not limited thereto.

The antioxidation component which serves to prevent the fabric from being aged may be an antioxidation component with an ability to significantly reduce or prevent the destruction and depletion of the function and structure of the fabric damaged by oxidation, such as extracts derived from natural materials such as animals, plants, minerals, and the like, fermented extracts, amino acids, peptides, proteins, and the like, but the present invention is not limited thereto. For example, the antioxidation component may be one or more selected from the group consisting of acetamido caproic acid, acetyl benzoyloxy prasterone, acetylcysteine, 2-acetyl-hydroquinone, adamantanylcarboxamido hydroxylbenzamide, aminoethanesulfinic acid, aminopropyl ascorbyl phosphate, angoroside C, anserine, apigenin, arbutin, alpha-arbutin, ascorbic acid, asiaticoside, benzoguanamine, butyl-hydroxyanisol (BHA), butylated hydroxytoluene (BHT), bis-hydroxyethyl tocopherylsuccinoylamido hydroxypropane, bis-(tetramethyl hydroxypiperidinyl)sebacate), butylated xylenol, t-butylbenzamido hydroxylbenzamide, 4-butylresorcinol, caffeic acid, calcium ascorbate, carnosic acid, carotenoids, chitosan ascorbate, chlorogenic acid, cobalt DNA, copper adenosine triphosphate (ATP), copper pyridoxal 5-phosphate, curcumin, cysteine, cysteine hydrochloride (HCl), decapeptide-6, decapeptide-7, decursinol, decyl mercaptomethylimidazole, diamylhydroquinone, di-t-butylhydroquinone, dicetyl thiodipropionate, dicyclopentadiene/t-butylcresol copolymer, digalloyl trioleate, diisooctyl sebacate, dilauryl thiodipropionate, dimethoxybenzamido phenylhydroxylacetamide, dimethoxy di-p-cresol, dimethylmethoxy chromanol, dimyristyl thiodipropionate, dioleyl tocopheryl methylsilanol, diosmine, diretinyl ether, disodium ascorbyl sulfate, distearyl thiodipropionate, ditridecyl thiodipropionate, dodecyl gallate, *dunaliella* bardawil powder, ellagic acid, epigallocatechin gallate, ergothioneine, *Eriobotrya japonica* leaf protoplasts, erythorbic acid, ethylbisiminomethylguaiacol manganese chloride, ethyl ferulate, ethylhexyl ferulate, ferulic acid, feruloyl soy glycerides, furfuryl palmitate, genistein glucoside, *Ginkgo* leaf terpenoids, glucosylrutin, glyceryl chromonyl ether, glyceryl diferulate, hesperetin, hexyloxy trimethylphenol, honokiol, hydrolyzed proanthocyanidin, hydroquinone, p-hydroxyanisole, hydroxydecyl ubiquinone, hydroxylamine hydrochloride (HCl), hydroxylamine sulfate, hydroxyphenyl dihydroxybenzamide, inositol hexaniacinate hexaascorbate, isooctyl caprylate/caprate, isooctyl thioglycolate, isoquercitrin, kaempferol, kojic acid, kojyl glucoside, kojyl methylenedioxycinnamate, kou-cha ekisu, lycopene, madecassoside, magnesium ascorbate, magnolol, manganese adenosine triphosphate (ATP), matrine, melatonin, methoxy PEG-7 ascorbic acid, methoxytrimethylphenyl dihydroxyphenyl propanol, methyl di-t-butyl hydroxyhydrocinnamate, methylene di-t-butylcresol, methyl methacrylate/trimethoxysilylpropyl methacrylate crosspolymer, methyl myristic acid, niacinamide hydroxybenzoate, nictoflorin, nordihydroguaiaretic acid, octanicotinoyl epigallocatechin gallate, octapeptide-4, oligopeptide-28, paeonol, palmatine, PEG/PPG-2/5 tocopheryl ether, perillyl alcohol, phenethyl caffeate, phenylethyl resorcinol, phenylthioglycolic acid, phloretin, phloroglucinol, piceatannol, piperlonguminine, porphyridium polysaccharide, potassium ascorbyl tocopheryl phosphate, potassium sulfite, PPG-2 tocophereth-5, propyl gallate, protocatechuic aldehyde, puerarin, pyridoxine hydroxybenzoate, pyridyloxide t-butylnitrone, quercetin, resacetophenone, resorcinol, resveratrol, retinyl formyl aspartamate, rosmarinic acid, rutin, rutinyl succinate, ryokucha ekisu, salnacedin, sodium ascorbate, sodium sulfite, sodium tocopheryl phosphate, sodium erythorbate, sodium phosphono-pyridoxylidenerhodanine, sodium thioglycolate, sodium zinc histidine dithiooctanamide, sorbityl furfural, stearyl gallate, succinoyl ascorbate pentapeptide-6, tangeritin, tert-butylhydroquinone (TBHQ), tetrabutyl ethylidinebisphenol, tetrahydrodemethoxydiferuloylmethane, tetrahydrocurcumin diacetate, tetrahydrodiferuloylmethane, tetramethylbutyl dihydroxybenzamide, tetramethylchromanol glucoside, thioctic acid, thiodiglycol, thiolactic acid, thiosalicylic acid, thioaurine, thymol trimethoxycinnamate, tococysteamide, tocophereth-5, tocopherols, tocophersolan, tocopheryl acetate, tocoquinone, toluene, o-tolyl biguanide, totarol, tripropylene glycol, tris-BHT mesitylene, tris(nonylphenyl)phosphite, trisodium ascorbyl isopalmitate phosphate, tyrosyl histidine hydrochloride (HCl), ubiquinol, ubiquinone, *Ulva lactuca* powder, uuron-cha ekisu, xylyl dibutylbenzofuranone, zinc adenosine triphosphate (ATP), zinc dibutyldithiocarbamate, zinc fructose diphosphate, zinc pyridoxal 5-phosphate, and a derivative thereof, but the present invention is not limited thereto.

The component for blocking ultraviolet rays, which is a main component having effects of preventing damage caused by light and maintaining the color of the fabric may include an ultraviolet ray absorbent such as a p-aminobenzoic acid derivative, a cinnamic acid derivative, a salicylic acid derivative, a benzophenone derivative, or the like, an ultraviolet ray dispersing agent such as titanium oxide, zinc oxide, or the like, a resin such as a cellulose-based polymer, a PVP/alpha-olefin-based polymer, an acrylate polymer, a silicone resin, a fluorine-modified silicone resin, or the like, and a polymer film-forming agent. A component having a substantial function of blocking ultraviolet rays may be, for example, one or more selected from the group consisting of cinnamic acid, glyceryl PABA, drometrizole, digalloyl trioleate, 3-(4-methylbenzylidene)camphor, menthyl anthranilate, benzophenone-3, benzophenone-4, benzophenone-8, butylmethoxy benzoylmethane, cinoxate, adenine riboside, octocrylene, octyl dimethyl PABA, octyl methoxycinnamate, octyl salicylate, octyl triazone, para-aminobenzoic acid, 2-benzimidazole-5-sulfonic acid, homosalate, zinc oxide, titanium dioxide, isoamyl-p-methoxycinnamate, bisethylhexyloxyphenol methoxyphenyltriazine, disodium phenyl dibenzimidazole tetrasulfonate, amodi-drometrizole trisiloxane, diethylhexyl butamido triazone, polysilicon-15 (dimethicodiethylbenzalmalonate), methylene bis-benzotriazolyl tetramethylbutylphenol, terephthalylidene dicamphor sulfonic acid, and a salt thereof, but the present invention is not limited thereto.

The skin surface-modifying component or the hair surface-modifying component may be used at a content of 0.0001 to 50 parts by weight, 0.001 to 30 parts by weight, 0.01 to 10 parts by weight, or 0.1 to 5 parts by weight with respect to 100 parts by weight of the entire composition. When it is used at a content of less than 0.0001 part by weight, there is a limitation in providing the effect of an active ingredient, and when it is used at a content of greater than 50 parts by weight, there is a problem in formulation and the stability of formulation over time, and the components may act as a component which does not react and is lost.

The fabric care component may be used at a content of 0.0001 to 50 parts by weight, 0.001 to 30 parts by weight, 0.01 to 10 parts by weight, or 0.1 to 5 parts by weight with respect to 100 parts by weight of the entire composition. When the fabric care component is used at a content of less than 0.0001 part by weight, there is a limitation in exhibiting effective performance, and when the fabric care component is used at a content of greater than 50 parts by weight, there is a problem in formulation and the stabilization of a formulation.

In particular, in the present invention, the skin surface-modifying component, the hair surface-modifying component, or the fabric care component includes a carboxyl group, a hydroxyl group, a phosphate group, or an amine group in a molecule thereof so that reaction efficiency with a carbodiimide-based compound may be increased.

In addition, in the present invention, the skin surface-modifying component, the hair surface-modifying component, or the fabric care component may have a functional group capable of covalently bonding with a protein residue in a skin, hair, or fabric surface, or may further include a component containing a functional group capable of covalently bonding with a protein residue in a skin, hair, or fabric surface.

The functional group capable of covalently bonding with a protein residue may be one or more selected from the group consisting of carbodiimides, imidoesters, aryl azides, diazirines, hydroxymethyl phosphine, pentafluorophenyl esters, pyridyl disulfide, sulfo-hydroxysuccinimide esters, alkoxyamines, hydrazides, haloacetyls, azide, carbonates, aldehydes, propionaldehyde, butylaldehyde, nitrophenyl carbonate, aziridines, isocyanate, thiocyanate, epoxides, tresylates, succinimide, hydroxysuccinimidyl esters, imidazole, oxycarbonylamidazole, imines, thiols, maleimide, vinylsulfone, ethyleneimine, thioethers, acrylonitrile, acrylic or methacrylic acid ester, disulfides, and ketones, but the present invention is not limited thereto.

In addition, the functional group may react with a thiol, hydroxyl, carboxyl, or amine residue of an amino acid constituting a protein.

In a preferable embodiment of the surface modification composition or the fabric care composition according to the present invention, a skin, hair, or fabric surface-modifying component having a carboxyl group is directly prepared in the form of a reactive ester surface-modifying component with bioreactivity, or an excessive amount of an amino acid (e.g., asparaginic acid or glutamic acid) present in the skin, hair, or fabric is subjected to reactive esterification, and thus prepared in the form of an ester with reactivity (reactive surface-modifying component) using a carbodiimide-based compound which a surface-modifying component having an amine group can target to increase reaction efficiency, and as a result, an effect thereof may be significantly increased. Also, a surface-modifying component or a fabric care component, which targets other amino acids or has a functional group such as carbodiimides, imidoesters, aryl azides, diazirines, hydroxymethyl phosphine, pentafluorophenyl esters, pyridyl disulfide, sulfo-hydroxysuccinimide esters, hydroxysuccinimide esters, alkoxyamines, hydrazides, haloacetyls, or azide, which reinforces the carbodiimide reaction, in a molecule thereof, may be additionally used to further increase an effect thereof.

In a more preferable embodiment, a carbodiimide-based compound represented by Chemical Formula 1 may primarily react with a molecule of a surface-modifying component having a carboxyl group or a protein surface of the skin, hair, or fabric to form a reactive ester, and then the reactive ester functional group thus formed may react with a surface-modifying component including amines in a molecule thereof or with amines in a skin surface to obtain an excellent surface modification effect. When the reaction is performed at preferably pH 2 to 10, more preferably pH 3 to 9, and most preferably pH 4 to 6.5, that is, in an acidic to weak acidic aqueous solution, reaction efficiency may be maximized. The reaction is completed in 1 to 30 minutes.

In Reaction Scheme 1 below, a schematic diagram of a reaction, in which a molecule of a skin surface-modifying component including a carboxyl group primarily reacts with a carbodiimide-based compound to form a reactive ester, and then the reactive ester thus formed reacts with a biological amino acid having an amine residue to form a covalent bond, is illustrated.

[Reaction Scheme 1]

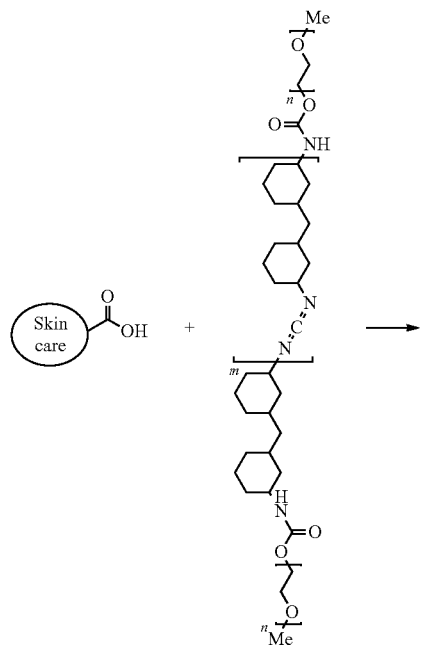

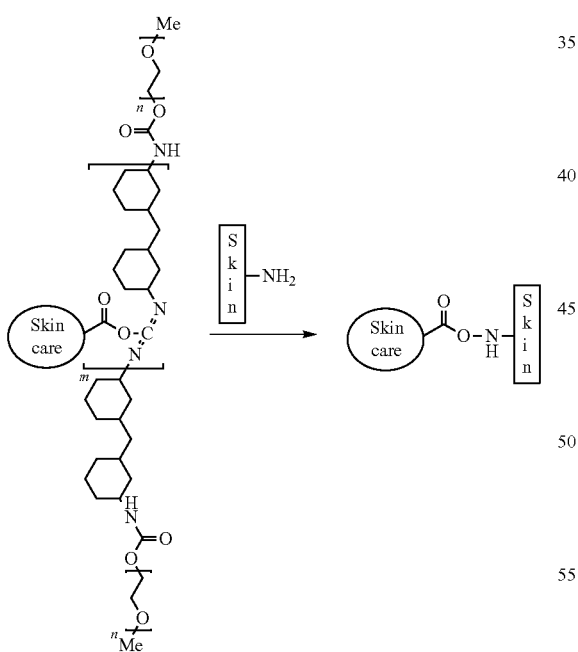

[Reaction Scheme 2]

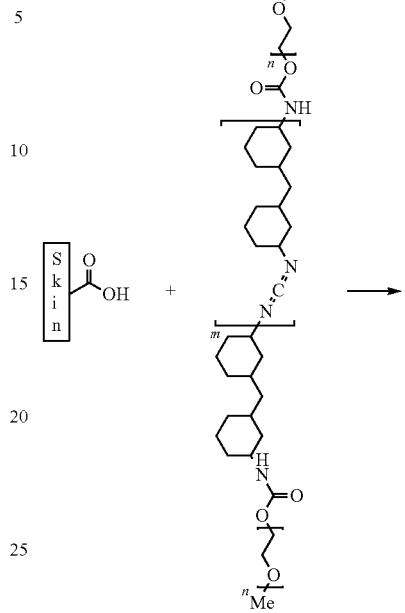

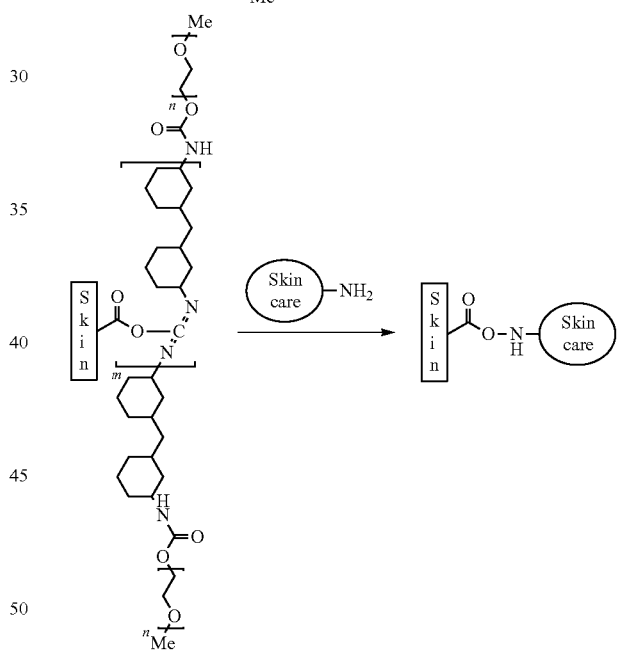

In Reaction Scheme 2 below, a schematic diagram of a reaction, in which asparaginic acid and glutamic acid, which are biological amino acids in a protein surface of skin and have a carboxyl group, primarily react with a carbodiimide-based compound to form a reactive ester, and then the reactive ester thus formed reacts with a skin surface-modifying component having an amine residue to form a covalent bond, is illustrated.

Since the efficiency of a reaction between a protein of skin and a skin surface-modifying component is increased due to a carbodiimide-based compound, the reactive skin surface-modifying component bonded to the skin may be not easily detached during general washing with a cleanser, a soap, or the like, but almost permanently attached to the skin.

In Reaction Scheme 3 below, a schematic diagram of a reaction, in which a molecule of a hair surface-modifying component having a carboxyl group primarily reacts with a carbodiimide-based compound to form a reactive ester, and then the reactive ester thus formed reacts with a biological amino acid having an amine residue to form a covalent bond, is illustrated.

[Reaction Scheme 3]

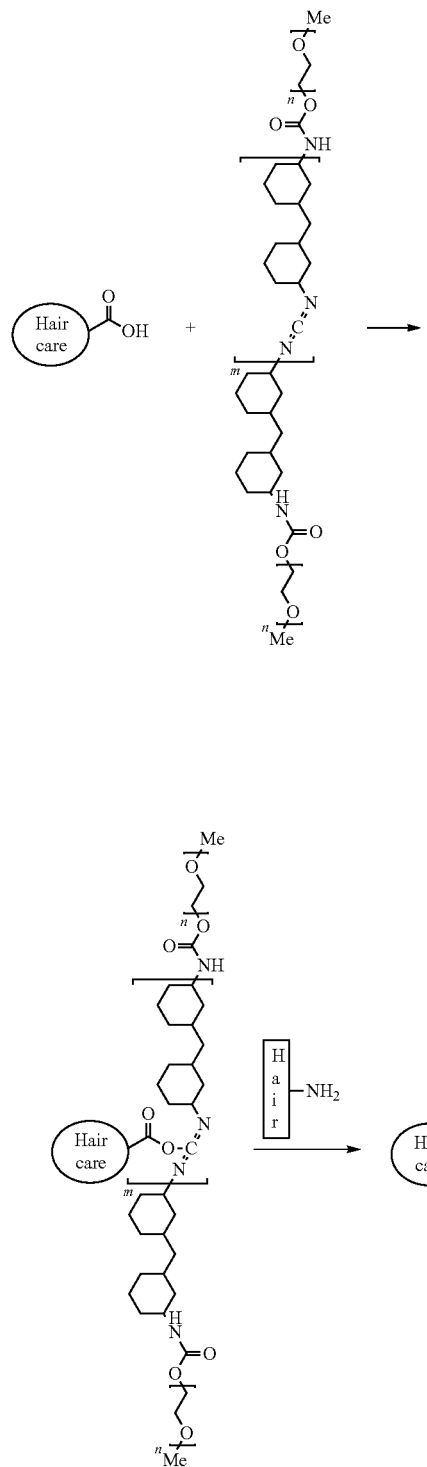

[Reaction Scheme 4]

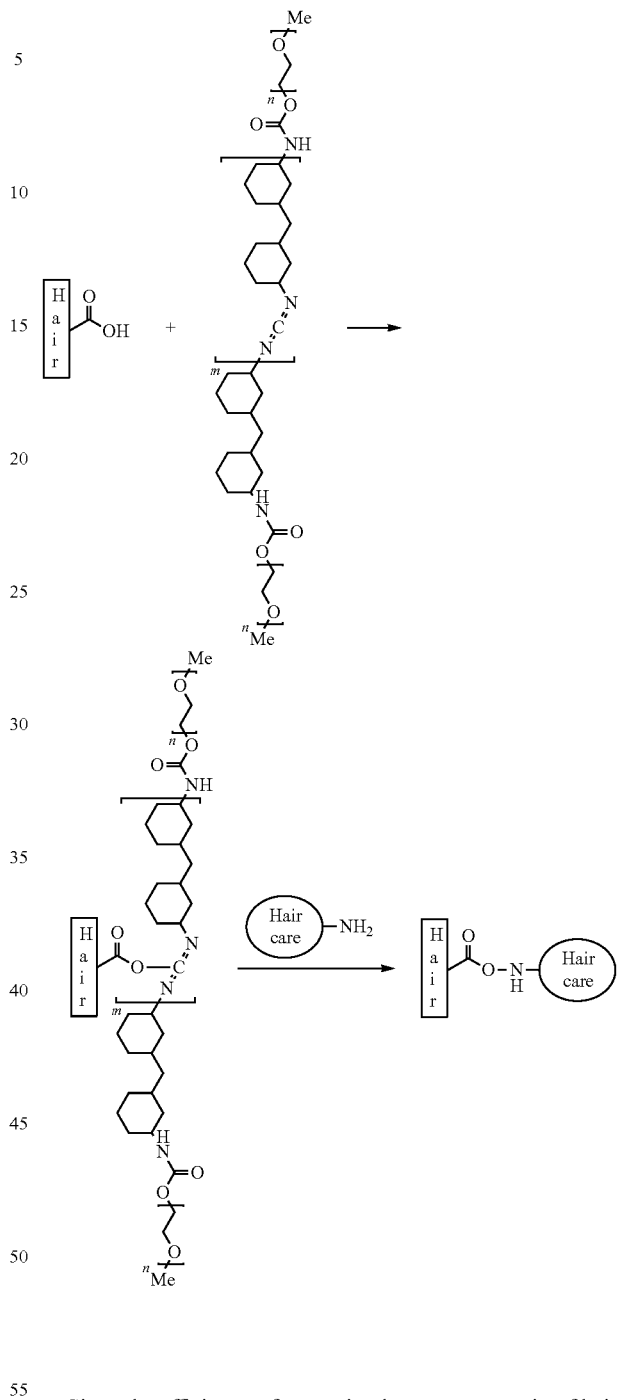

In Reaction Scheme 4 below, a schematic diagram of a reaction, in which asparaginic acid and glutamic acid, which are biological amino acids in a protein surface of hair and include a carboxyl group, primarily react with a carbodiimide-based compound to form a reactive ester, and then the reactive ester thus formed reacts with a hair surface-modifying component having an amine residue to form a covalent bond, is illustrated.

Since the efficiency of a reaction between a protein of hair and a hair surface-modifying component is increased due to a carbodiimide-based compound, a reactive hair surface-modifying component bonded to the hair may be not easily detached during general washing with a shampoo, a soap, or the like, but almost permanently attached to the hair.

In Reaction Scheme 5 below, a schematic diagram of a reaction, in which a molecule of a fabric care component having a carboxyl group primarily reacts with a carbodiimide-based compound to form a reactive ester, and then the reactive ester thus formed reacts with an amine residue to form a covalent bond, is illustrated.

[Reaction Scheme 5]

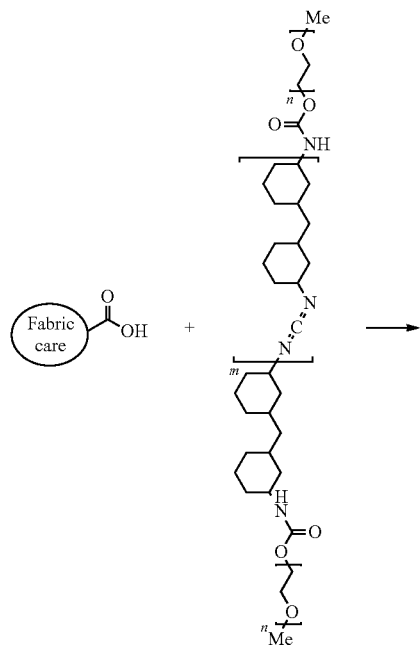

[Reaction Scheme 6]

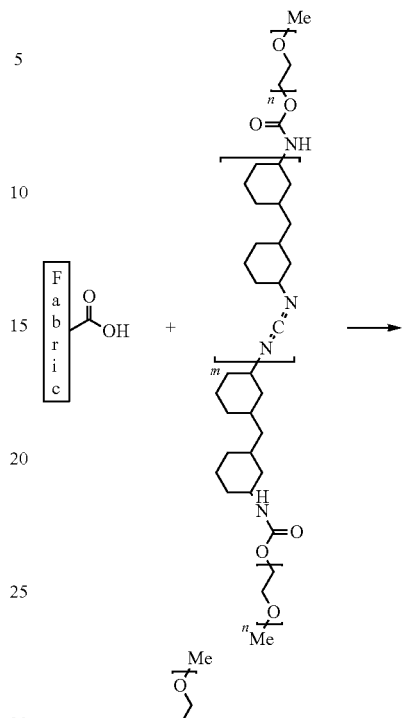

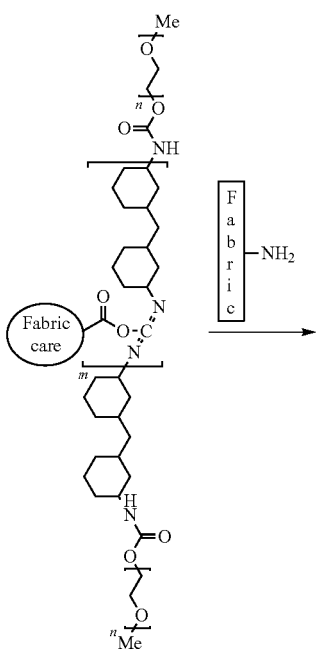

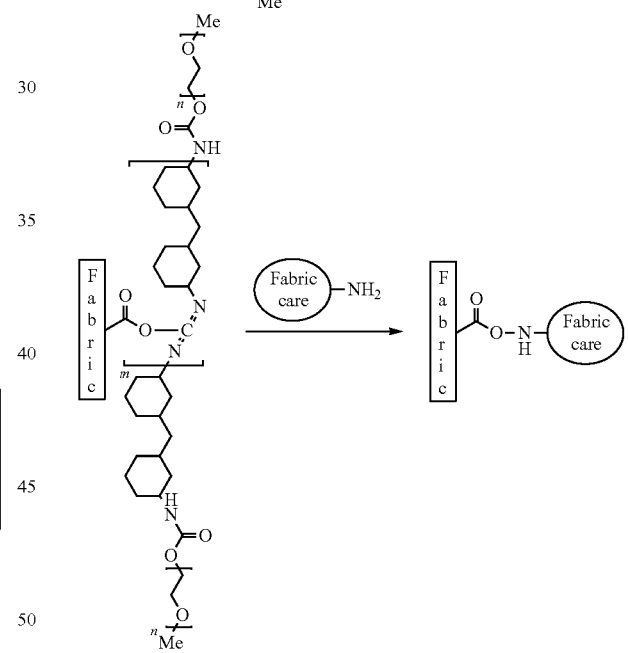

In Reaction Scheme 6 below, a schematic diagram of a reaction, in which a carboxyl group in a fabric surface primarily reacts with a carbodiimide-based compound to form a reactive ester, and then the reactive ester thus formed reacts with a fabric care component having an amine residue to form a covalent bond, is illustrated.

Since the efficiency of a reaction between a reactive residue in a fabric and a fabric care component is increased due to a carbodiimide-based compound; a reactive fabric care component bonded to the fabric may be not easily detached during general washing with a detergent, a soap, or the like, but almost permanently attached to the fabric.

In addition, in the present invention, the skin surface-modifying component, the hair surface-modifying component, or the fabric care component may further include a reactive surface-modifying component (care component) bonded with a functional group capable of covalently bonding with one or more proteins selected from the group consisting of carbodiimides, imidoesters, aryl azides, diazirines, hydroxymethyl phosphine, pentafluorophenyl esters, pyridyl disulfide, sulfo-hydroxysuccinimide esters, alkoxyamines, hydrazides, haloacetyls, azide, carbonates, aldehydes, propionaldehyde, butylaldehyde, nitrophenyl carbonate, aziridines, isocyanate, thiocyanate, epoxides, tresylates, succinimide, hydroxysuccinimidyl esters, imidazole, oxycarbonylamidazole, imines, thiols, maleimide, vinylsulfone, ethyleneimine, thioethers, acrylonitrile, acrylic or methacrylic acid ester, disulfides, and ketones.

For example, as shown in Reaction Schemes 1, 3, and 5, a surface-modifying component (care component) bonded with a carbodiimide group, which is produced by primarily reacting a carbodiimide-based compound, may be included. Also, the present invention may provide a composition for surface modification including the reactive surface-modifying component (care component).

In order to additionally increase an effect of the composition for surface modification (care component) according to the present invention in the formulation of the composition into cosmetics, the composition may be used in combination with a fatty acid such as palmitic acid, stearic acid, and the like, a fatty alcohol, a cationized polymer such as a cationic surfactant including linear/branched long-chain alkyl quaternary ammonium salts or the like, cationic cellulose, cationic guar, cationic polyvinylpyrrolidone, and the like, a silicone, or the like for ease of formulation. Also, in order to formulate the composition as a cosmetic, components such as a solvent, a surfactant, a thickening agent, a stabilizer, a preservative, a coloring agent, a pH controlling agent, a chelating agent, a coloring agent, a pearlescent agent, an appearance improving agent, a pigment, a particulate material, and the like may be additionally included. The component for formulation may be used at a content of 0.0001 to 30 parts by weight with respect to 100 parts by weight of the entire composition.

The composition for skin surface modification according to the present invention includes a skin surface-modifying component including a functional group, and thus may be used in the skin care product treatment. The skin care products generally are products for freshening skin up and protecting skin, and may include all formulations that can be applied to skin, including fundamental cosmetics (toners, serums, essences, lotions, creams, and the like), color cosmetics (makeup base, foundation, face powder, eye shadow, lip gloss, lipstick, lip balm, and the like), cleansing cosmetics (foam cleansing, cleansing oils, cleansing lotions, cleansing creams, cleansing gels, packs, masks, soaps, cleansing tissues, and the like), sun care cosmetics (sun sprays, sunscreens, sunblocks, sun gels, and the like), body care cosmetics (body cleansers, body lotions, shower gels, bath salts, body creams, body oils, and the like), and fingernail and toenail care cosmetics (nail polishes, nail hardeners, coats, removers, nail dyes, nail tattoos, cuticle removers and oils).

The composition for hair surface modification according to the present invention includes a hair surface-modifying component including a functional group, and thus may be used in the hair care product treatment. The hair care products may include all formulations that can be applied to hair, including shampoos, conditioners, treatments, hair packs, hair essences, hair waxes, hair gels, hair sprays, hair mousses, hair dyes, hair bleaching products, hair perm products, hair tonics, hair regrowth products, hair growth promoters, hair root and scalp activators, hair styling products, coating products, film forming agents, and the like.

The composition for fabric care according to the present invention includes a fabric care component including a functional group, and thus may be used in the fabric care product treatment. The fabric care products may generally include fabric softeners, liquid detergents, powdered detergents, sheet type detergents, fabric dyes, fabric treatments, fabric conditioners, bleaching products, stain removers, fabric styling products, ironing aids, preservatives, and the like.

More preferably, the composition for surface modification (care composition) according to the present invention includes a carbodiimide-based compound, and simultaneously includes a skin surface-modifying component including a reactive functional group. If the activity of the formulation is degraded when the formulation is in an aqueous environment, its activity is more easily maintained by being in a non-aqueous form. Also, a reaction of the formulation may be induced by mixing with a buffer solution immediately before use to adjust a pH or bringing in contact with water in a washing process. Examples of a non-aqueous form include liquid types, sheet types, powder types, tablet types, oils, wax, ampoules, gels, and the like, which are commonly used as a non-aqueous cosmetic formulation. In addition, the composition may be prepared in the form of a single formulation in which the carbodiimide-based compound and the surface-modifying component (care component) are encapsulated, or in the form of two distinct formulations in which the carbodiimide-based compound and the surface-modifying component (care component) are separated from each other. Additionally, a method of blocking a derivative of the reactive functional group and the surface-modifying component (care component) bonded to each other from moisture through encapsulation may be used.

In order to increase a surface modification effect (care effect) of the composition for surface modification (care composition) including a functional group according to the present invention, a dibasic acid ester oil such as dioctyl succinate, dioctyl adipate, diethyl sebacate, or the like, a polyol, polyethylene glycol, propylene glycol, hexylene glycol, butanediol and an isomer thereof, glycerol, benzyl alcohol, or ethoxydiglycol and a derivative thereof may be used. The solvent mentioned above serves to increase permeability into the skin, hair, or fabric and is used as a solvent for a poorly soluble material. More preferably, diethyl sebacate, ethoxydiglycol, bis-ethoxydiglycol cyclohexane 1,4-dicarboxylate, or the like is used as a solvent used to increase an effect of maintaining the activity of the surface-modifying component (care component) including a functional group.

BEST MODE

Hereinafter, the present invention will be described in detail with reference to examples. However, the following examples are illustrative of the present invention, and the present invention is not limited to the following examples.

Comparative Examples 1 to 8 and Examples 1 to 4: Preparation of Body Cleanser

Compositions for a body cleanser, which contain sphingosine, amodimethicone, hyaluronic acid, or Red No. 227, which is generally used in a body cleanser as a conditioning component, a component for imparting gloss to skin, a skin moisturizing component, or a dye for skin and nails, respectively, in compositions and quantities as listed in Table 1 below, and include no carbodiimide-based polymer (Comparative Examples 1 to 4); benzene, 1,3-bis(1-isocyanato-1-methylethyl)-, homopolymer, polyethylene glycol mono-Me-ether-blocked as a carbodiimide-based polymer (Comparative Examples 5 to 8); or 1,1'-methylene-bis-(3-isocyanatocyclohexane)-, homopolymer, polyethylene glycol mono-Me-ether-blocked polymer which is a carbodiimide-based polymer of the present invention (Examples 1 to 4), were prepared.

TABLE 1

| Composition (wt %) | Comparative Example 1 | Comparative Example 2 | Comparative Example 3 | Comparative Example 4 | Comparative Example 5 | Comparative Example 6 | Comparative Example 7 | Comparative Example 8 | Example 1 | Example 2 | Example 3 | Example 4 |
|---|---|---|---|---|---|---|---|---|---|---|---|---|
| Water | 55 | 55 | 55 | 55 | 54 | 54 | 54 | 54 | 54 | 54 | 54 | 54 |
| Polyquaternium-7 | 0.5 | 0.5 | 0.5 | 0.5 | 0.5 | 0.5 | 0.5 | 0.5 | 0.5 | 0.5 | 0.5 | 0.5 |
| EDTA 4Na | 0.05 | 0.05 | 0.05 | 0.05 | 0.05 | 0.05 | 0.05 | 0.05 | 0.05 | 0.05 | 0.05 | 0.05 |
| Lauric acid | 3 | 3 | 3 | 3 | 3 | 3 | 3 | 3 | 3 | 3 | 3 | 3 |
| Myristic acid | 4 | 4 | 4 | 4 | 4 | 4 | 4 | 4 | 4 | 4 | 4 | 4 |
| Sodium lauryl ether (2 moles) sulfate (30%) | 20 | 20 | 20 | 20 | 20 | 20 | 20 | 20 | 20 | 20 | 20 | 20 |
| Cocamidopropyl betaine (30%) | 15 | 15 | 15 | 15 | 15 | 15 | 15 | 15 | 15 | 15 | 15 | 15 |
| Fragrance | 0.9 | 0.9 | 0.9 | 0.9 | 0.9 | 0.9 | 0.9 | 0.9 | 0.9 | 0.9 | 0.9 | 0.9 |
| Sphingosine | 1 | — | 1 | — | 1 | — | — | — | 1 | — | — | — |
| Amodimethicone | — | 1 | — | — | — | 1 | — | — | — | 1 | — | — |
| Hyaluronic acid | — | — | 1 | — | — | — | 1 | — | — | — | 1 | — |
| Red No. 227 | — | — | — | 1 | — | — | — | 1 | — | — | — | 1 |
| Benzene, 1,3-bis(1-isocyanato-1-methylethyl)-, homopolymer, polyethylene glycol mono-Me-ether-blocked | — | — | — | — | 1 | 1 | 1 | 1 | — | — | — | 1 |
| 1,1'-methylene-bis-(3-isocyanatocyclohexane)-, homopolymer, polyethylene glycol mono-Me-ether-blocked | — | — | — | — | — | — | — | — | 1 | 1 | 1 | 1 |
| pH controlling agent | Suitable amount | Suitable amount | Suitable amount | Suitable amount | Suitable amount | Suitable amount | Suitable amount | Suitable amount | Suitable amount | Suitable amount | Suitable amount | Suitable amount |
| Total | 100 | 100 | 100 | 100 | 100 | 100 | 100 | 100 | 100 | 100 | 100 | 100 |

Experimental Example 1: Assessment of Conditioning, Gloss, Moisturizing, and Dyeing Effects Each of the compositions for a body cleanser according to Comparative Examples 1 to 8 and Examples 1 to 4 was used to wash a pig skin sample with a size of 2 cm (width)×2 cm (length) ten times to induce surface modification, and each skin sample was washed three times with a 15% sodium lauryl ethyl sulfate solution (surfactant) to remove a component which was not covalently bonded but just adsorbed onto the skin. Afterward, the skin samples thus treated were compared in terms of a skin conditioning effect (sensory evaluation; five-level scale [5: very good, 4: slightly good, 3: moderate, 2: slightly poor, 1: very poor]; n=30), an increment in gloss determined by measuring the reflectivity of light with a skin glossmeter, moisturizing using a skin conditioner, and redness measured with a color meter with those of untreated skin samples, the result of which is shown in Table 2 below.

TABLE 2

| Classification | Comparative Example 1 | Comparative Example 2 | Comparative Example 3 | Comparative Example 4 | Comparative Example 5 | Comparative Example 6 | Comparative Example 7 | Comparative Example 8 | Example 1 | Example 2 | Example 3 | Example 4 |
|---|---|---|---|---|---|---|---|---|---|---|---|---|
| Conditioning effect | 2.7 | — | — | — | 3.9 | — | — | — | 4.7 | — | — | — |
| Increment in gloss (%) | — | 3.5 | — | — | — | 17.6 | — | — | — | 46.3 | — | — |
| Increment in contained water (%) | — | — | 2.3 | — | — | — | 26.5 | — | — | — | 48.7 | — |
| Increment in redness (%) | — | — | — | 15.9 | — | — | — | 32.3 | — | — | — | 48.6 |

As shown in Table 2, it was confirmed that Examples 1 to 4 including a carbodiimide-based polymer of the present invention exhibited significantly excellent effects of skin conditioning and an increment in gloss, moisturizing, and redness caused by dyeing compared to Comparative Examples 1 to 8.

Experimental Example 2

Compositions for a body cleanser were prepared using the same compositions as in Examples 1 to 4 except that compounds listed in Table 3 below were used instead of the carbodiimide-based compounds used in Examples 1 to 4. For the compositions for a body cleanser, a surface modification effect was assessed through the same method as in Experimental Example 1, the result of which is shown in Table 3 below.

TABLE 3

| Compound | Skin conditioning (five-level scale) | Increment in skin gloss (%) | Increment in contained water (%) | Increment in redness (%) |
|---|---|---|---|---|
| 1,3-Bis(isocyanatomethyl)cyclohexane-, homopolymer, polyethylene glycol mono-Me-ether-blocked | 4.3 | 43.6 | 46.7 | 46.3 |
| Benzene-1,3-diisocyanate-, homopolymer, polyethylene glycol mono-Me-ether-blocked | 4.1 | 43.2 | 45.3 | 44.2 |
| Hexamethylene diisocyanate-, homopolymer, polyethylene glycol mono-Me-ether-blocked | 4.0 | 42.2 | 44.6 | 44.1 |

TABLE 3-continued

| Compound | Skin conditioning (five-level scale) | Increment in skin gloss (%) | Increment in contained water (%) | Increment in redness (%) |
|---|---|---|---|---|
| PEG 600 diisocyanate-, homopolymer, polyethylene glycol mono-Me-ether-blocked | 4.6 | 45.7 | 47.3 | 47.6 |
| Diphenylmethane-2,2'-diisocyanate-, homopolymer, polyethylene glycol mono-Me-ether-blocked | 4.5 | 45.0 | 46.9 | 46.6 |
| Isophorone diisocyanate-, homopolymer, polyethylene glycol mono-Me-ether-blocked | 4.3 | 44.5 | 45.2 | 46.0 |

Comparative Examples 9 to 14 and Examples 5 to 7: Preparation of Body Cleanser Composition Compositions for a body cleanser, which contain niacinamide, hyaluronic acid, or salicylic acid, which is generally used as a skin whitening component, an anti-wrinkle component, or a keratin care component, respectively, in compositions and quantities as listed in Table 4 below, and include no carbodiimide-based polymer (Comparative Examples 9 to 11); benzene, 1,3-bis(1-isocyanato-1-methylethyl)-, homopolymer, polyethylene glycol mono-Me-ether-blocked as a carbodiimide-based (Comparative Examples 12 to 14); or 1,1'-methylene-bis-(3-isocyanatocyclohexane)-, homopolymer, polyethylene glycol mono-Me-ether-blocked polymer which is a carbodiimide-based polymer of the present invention (Example 5 to 7), were prepared.

TABLE 4

| Composition (wt %) | Comparative Example 9 | Comparative Example 10 | Comparative Example 11 | Comparative Example 12 | Comparative Example 13 | Comparative Example 14 | Example 5 | Example 6 | Example 7 |
|---|---|---|---|---|---|---|---|---|---|
| Water | 55 | 55 | 55 | 54 | 54 | 54 | 54 | 54 | 54 |
| Polyquaternium-7 | 0.5 | 0.5 | 0.5 | 0.5 | 0.5 | 0.5 | 0.5 | 0.5 | 0.5 |
| EDTA 4Na | 0.05 | 0.05 | 0.05 | 0.05 | 0.05 | 0.05 | 0.05 | 0.05 | 0.05 |
| Lauric acid | 3 | 3 | 3 | 3 | 3 | 3 | 3 | 3 | 3 |
| Myristic acid | 4 | 4 | 4 | 4 | 4 | 4 | 4 | 4 | 4 |
| Sodium lauryl ether (2 moles) sulfate (30%) | 20 | 20 | 20 | 20 | 20 | 20 | 20 | 20 | 20 |
| Cocamidopropyl betaine (30%) | 15 | 15 | 15 | 15 | 15 | 15 | 15 | 15 | 15 |
| Fragrance | 0.9 | 0.9 | 0.9 | 0.9 | 0.9 | 0.9 | 0.9 | 0.9 | 0.9 |
| Niacinamide | 1 | — | — | 1 | — | — | 1 | — | — |
| Hyaluronic acid | — | 1 | — | — | 1 | — | — | 1 | — |
| Salicylic acid | — | — | 1 | — | — | 1 | — | — | 1 |
| Benzene,1,3-bis(1-isocyanato-1-methylethyl)-, homopolymer, polyethylene glycol mono-Me-ether-blocked | — | — | — | 1 | 1 | 1 | — | — | — |
| 1,1'-methylene-bis-(3-isocyanato-cyclohexane)-, homopolymer, polyethylene glycol mono-Me-ether-blocked | — | — | — | — | — | — | 1 | 1 | 1 |

TABLE 4-continued

| Composition (wt %) | Comparative Example 9 | Comparative Example 10 | Comparative Example 11 | Comparative Example 12 | Comparative Example 13 | Comparative Example 14 | Example 5 | Example 6 | Example 7 |
|---|---|---|---|---|---|---|---|---|---|
| pH controlling agent | Suitable amount | Suitable amount | Suitable amount | Suitable amount | Suitable amount | Suitable amount | Suitable amount | Suitable amount | Suitable amount |
| Total | 100 | 100 | 100 | 100 | 100 | 100 | 100 | 100 | 100 |

Experimental Example 3: Assessment of Whitening, Wrinkle and Keratin Improvement Effect Each group of 10 panelists who thought that they needed to manage whitening, a wrinkle, and keratin was asked to use each of the compositions according to Comparative Examples 9 to 14 and Examples 5 to 7 daily for 20 days and then use a general body cleanser for 10 days. In this case, satisfaction in terms of the degree of improvement immediately after 20 days of use and the persistence of the effect after 10 days was sensorially evaluated based on a five-level scale [5: very good, 4: slightly good, 3: moderate, 2: slightly poor, 1: very poor], the result of which is shown in Table 5 below.

TABLE 5

| Classification | Comparative Example 9 | Comparative Example 10 | Comparative Example 11 | Comparative Example 12 | Comparative Example 13 | Comparative Example 14 | Example 5 | Example 6 | Example 7 |
|---|---|---|---|---|---|---|---|---|---|
| Whitening (improvement, persistence) | (1.7, 2.5) | — | — | (3.5, 3.9) | — | — | (4.2, 4.5) | — | — |
| Wrinkle (improvement, persistence) | — | (1.9, 2.3) | — | — | (3.7, 4.0) | — | — | (4.5, 4.3) | — |
| Keratin (improvement, persistence) | — | — | (1.2, 1.9) | — | — | (3.4, 4.0) | — | — | (4.7, 4.3) |

As shown in Table 5, it was confirmed that Examples 5 to 7 including a carbodiimide-based polymer of the present invention exhibited significantly excellent effects of whitening, wrinkle care, and keratin care compared to Comparative Examples 9 to 14.

Experimental Example 4

Compositions for a body cleanser were prepared using the same compositions as in Examples 5 to 7 except that compounds listed in Table 6 below were used instead of the carbodiimide-based compound used in Examples 5 to 7. For the compositions for a body cleanser, a surface modification effect was assessed through the same method as in Experimental Example 3, the result of which is shown in Table 6 below.

TABLE 6

| Compound | Whitening (improvement, persistence) (five-level scale) | Wrinkle (improvement, persistence) (five-level scale) | Keratin (improvement, persistence) (five-level scale) |
|---|---|---|---|
| 1,3-Bis(isocyanatomethyl)cyclohexane-, homopolymer, polyethylene glycol mono-Me-ether-blocked | (4.0, 4.2) | (4.4, 4.0) | (4.4, 4.2) |
| Benzene-1,3-diisocyanate-, homopolymer, polyethylene glycol mono-Me-ether-blocked | (4.0, 4.1) | (4.1, 4.0) | (4.3, 4.1) |
| Hexamethylene diisocyanate-, homopolymer, polyethylene glycol mono-Me-ether-blocked | (3.9, 4.1) | (3.8, 4.0) | (4.0, 4.0) |

TABLE 6-continued

| Compound | Whitening (improvement, persistence) (five-level scale) | Wrinkle (improvement, persistence) (five-level scale) | Keratin (improvement, persistence) (five-level scale) |
|---|---|---|---|
| PEG 600 diisocyanate-, homopolymer, polyethylene glycol mono-Me-ether-blocked | (4.0, 4.2) | (4.3, 4.3) | (4.5, 4.2) |
| Diphenylmethane-2,2'-diisocyanate-, homopolymer, polyethylene glycol mono-Me-ether-blocked | (4.0, 4.1) | (4.2, 4.2) | (4.3, 4.2) |
| Isophorone diisocyanate-, homopolymer, polyethylene glycol mono-Me-ether-blocked | (3.9, 4.1) | (4.0, 4.1) | (4.2, 4.1) |

Comparative Examples 15 to 22 and Examples 8 to 11: Preparation of Shampoo Composition Shampoo compositions for hair, which contain stearylamidopropyl amine, phenyl amodimethicone, polylysine, or chitosan polymer, which is generally used in hair shampoo as a conditioning component, a conditioning component for imparting gloss to hair, a conditioning component for enhancing hair thickness, or a hair moisturizing component, respectively, in compositions and quantities as listed in Table 7 below, and include no carbodiimide-based polymer (Comparative Examples to 18); benzene, 1,3-bis(1-isocyanato-1-methylethyl)-, homopolymer, polyethylene glycol mono-Me-ether-blocked as a carbodiimide-based polymer (Comparative Examples 19 to 22); or 1,1'-methylene-bis-(3-isocyanatocyclohexane)-, homopolymer, polyethylene glycol mono-Me-ether-blocked which is a carbodiimide-based polymer of the present invention (Examples 8 to 11), were prepared.

TABLE 7

| Composition (wt %) | Comparative Example 15 | Comparative Example 16 | Comparative Example 17 | Comparative Example 18 | Comparative Example 19 | Comparative Example 20 | Comparative Example 21 | Comparative Example 22 | Example 8 | Example 9 | Example 10 | Example 11 |
|---|---|---|---|---|---|---|---|---|---|---|---|---|
| Water | 47 | 47 | 47 | 47 | 46 | 46 | 46 | 46 | 46 | 46 | 46 | 46 |
| Polyquaternium-10 | 0.5 | 0.5 | 0.5 | 0.5 | 0.5 | 0.5 | 0.5 | 0.5 | 0.5 | 0.5 | 0.5 | 0.5 |
| EDTA 4Na | 0.05 | 0.05 | 0.05 | 0.05 | 0.05 | 0.05 | 0.05 | 0.05 | 0.05 | 0.05 | 0.05 | 0.05 |
| Sodium lauryl ether (2 moles) sulfate (30%) | 35.0 | 35.0 | 35.0 | 35.0 | 35.0 | 35.0 | 35.0 | 35.0 | 35.0 | 35.0 | 35.0 | 35.0 |
| Cocamidopropyl betaine (30%) | 15.0 | 15.0 | 15.0 | 15.0 | 15.0 | 15.0 | 15.0 | 15.0 | 15.0 | 15.0 | 15.0 | 15.0 |
| Fragrance | 0.9 | 0.9 | 0.9 | 0.9 | 0.9 | 0.9 | 0.9 | 0.9 | 0.9 | 0.9 | 0.9 | 0.9 |
| Stearylamidopropyl amine | 1.0 | — | — | — | 1.0 | — | — | — | 1.0 | — | — | — |
| Phenylamodimethicone | — | 1.0 | — | — | — | 1.0 | — | — | — | 1.0 | — | — |
| Polylysine | — | — | 1.0 | — | — | — | 1.0 | — | — | — | 1.0 | — |
| Chitosan polymer | — | — | — | 1.0 | — | — | — | 1.0 | — | — | — | 1.0 |
| Benzene,1,3-bis(1-isocyanato-1-methylethyl)-, homopolymer, polyethylene glycol mono-Me-ether-blocked | — | — | — | — | 1.0 | 1.0 | 1.0 | 1.0 | — | — | — | — |
| 1,1'-methylene-bis-(3-isocyanatocyclohexane)-, homopolymer, polyethylene glycol mono-Me-ether-blocked | — | — | — | — | — | — | — | — | 1.0 | 1.0 | 1.0 | 1.0 |
| pH Controlling agent | Suitable amount | Suitable amount | Suitable amount | Suitable amount | Suitable amount | Suitable amount | Suitable amount | Suitable amount | Suitable amount | Suitable amount | Suitable amount | Suitable amount |
| Total | 100.0 | 100.0 | 100.0 | 100.0 | 100.0 | 100.0 | 100.0 | 100.0 | 100.0 | 100.0 | 100.0 | 100.0 |

Experimental Example 5: Assessment of Conditioning and Moisturizing Effects

Each of the shampoo compositions according to Examples 8 to 11 and Comparative Examples 15 to 22 was used to wash a hair tress having a length of 12 cm and a weight of 3 g ten times to induce surface modification, and each tress was washed three times with a 15% sodium lauryl ethyl sulfate solution (surfactant) to remove a component which was not covalently bonded but just adsorbed onto the hair. Afterward, the hair tresses thus treated were compared in terms of an increment in effects of conditioning (sensory evaluation; five-level scale [5: very good, 4: slightly good, 3: moderate, 2: slightly poor, 1: very poor]; n=30), gloss (determined by measuring reflectivity of light with a hair glossmeter), hair thickness (measured with an hair thickness measuring apparatus using a laser), and moisturizing (measured with a moisturizing measurement apparatus) with that of untreated hair tresses, the result of which is shown in Table 8 below.

TABLE 8

| Classification | Comparative Example 15 | Comparative Example 16 | Comparative Example 17 | Comparative Example 18 | Comparative Example 19 | Comparative Example 20 | Comparative Example 21 | Comparative Example 22 | Example 8 | Example 9 | Example 10 | Example 11 |
|---|---|---|---|---|---|---|---|---|---|---|---|---|
| Conditioning effect | 2.3 | — | — | — | 3.7 | — | — | — | 4.5 | — | — | — |
| Increment in gloss (%) | — | 1.2 | — | — | — | 28 | — | — | — | 53 | — | — |
| Increment in thickness (%) | — | — | 0.23 | — | — | — | 3.6 | — | — | — | 7.3 | — |
| Water contained in hair (%) | — | — | — | 10.3 | — | — | — | 17.2 | — | — | — | 25.6 |

As shown in Table 8, it was confirmed that Examples 8 to 11 including a carbodiimide-based polymer of the present invention exhibited significantly excellent effects of conditioning, improving gloss, enhancing hair thickness, and moisturizing compared to Comparative Examples 15 to 22.

Experimental Example 6

Shampoo compositions were prepared using the same compositions as in Examples 8 to 11 except that compounds listed in Table 9 below were used instead of the carbodiimide-based compound used in Examples 8 to 11. For the shampoo compositions, a surface modification effect was assessed through the same method as in Experimental Example 5, the result of which is shown in Table 9 below.

TABLE 9

| Compound | Hair conditioning (five-level scale) | Increment in hair gloss (%) | Increment in hair thickness (%) | Water contained in hair (%) |
|---|---|---|---|---|
| 1,3-Bis(isocyanatomethyl)cyclohexane-, homopolymer, polyethylene glycol mono-Me-ether-blocked | 4.3 | 48 | 7.2 | 24.3 |
| Benzene-1,3-diisocyanate-, homopolymer, polyethylene glycol mono-Me-ether-blocked | 4.1 | 45 | 6.9 | 24.0 |
| Hexamethylene diisocyanate-, homopolymer, polyethylene glycol mono-Me-ether-blocked | 4.0 | 44 | 6.6 | 23.6 |
| PEG 600 diisocyanate-, homopolymer, polyethylene glycol mono-Me-ether-blocked | 4.6 | 51 | 7.0 | 25.1 |
| Diphenylmethane-2,2'-diisocyanate-, homopolymer, polyethylene glycol mono-Me-ether-blocked | 4.4 | 49 | 6.8 | 24.8 |
| Isophorone diisocyanate-, homopolymer, polyethylene glycol mono-Me-ether-blocked | 4.4 | 47 | 6.6 | 24.0 |

Comparative Examples 23 to 26 and Examples 12 to 13: Preparation of Shampoo Composition Shampoo compositions, which contain Red No. 227 generally used in hair shampoo as a dyeing component or lauryl diamine with a structure capable of bonding split hair in compositions and quantities as listed in Table 10 below, and include no carbodiimide-based polymer (Comparative Examples 23 and 24); benzene, 1,3-bis(1-isocyanato-1-methylethyl)-, homopolymer, polyethylene glycol mono-Me-ether-blocked as a carbodiimide-based polymer (Comparative Examples 25 and 26); or 1,1'-methylene-bis-(3-isocyanatocyclohexane)-, homopolymer, polyethylene glycol mono-Me-ether-blocked polymer which is a carbodiimide-based polymer of the present invention (Examples 12 and 13), were prepared.

TABLE 10

| Composition (wt %) | Comparative Example 23 | Comparative Example 24 | Comparative Example 25 | Comparative Example 26 | Example 12 | Example 13 |
|---|---|---|---|---|---|---|
| Water | 47 | 47 | 46 | 46 | 46 | 46 |
| Polyquaternium-10 | 0.5 | 0.5 | 0.5 | 0.5 | 0.5 | 0.5 |
| EDTA 4Na | 0.05 | 0.05 | 0.05 | 0.05 | 0.05 | 0.05 |
| Sodium lauryl ether (2 moles) sulfate (30%) | 35.0 | 35.0 | 35.0 | 35.0 | 35.0 | 35.0 |
| Cocamidopropyl betaine (30%) | 15.0 | 15.0 | 15.0 | 15.0 | 15.0 | 15.0 |
| Fragrance | 0.9 | 0.9 | 0.9 | 0.9 | 0.9 | 0.9 |
| Red No. 227 | 1.0 | — | 1.0 | — | 1.0 | — |
| Lauryl diamine | — | 1.0 | — | 1.0 | — | 1.0 |
| Benzene, 1,3-bis (1-isocyanato-1-methylethyl)-, homopolymer, polyethylene glycol mono-Me-ether-blocked | — | — | 1.0 | 1.0 | — | — |
| 1,1'-methylene-bis-(3-isocyanatocyclohexane)-, homopolymer, polyethylene glycol mono-Me-ether-blocked | — | — | — | — | 1.0 | 1.0 |
| pH controlling agent | Suitable amount | Suitable amount | Suitable amount | Suitable amount | Suitable amount | Suitable amount |
| Total | 100.0 | 100.0 | 100.0 | 100.0 | 100.0 | 100.0 |

TABLE 11

| Classification | Comparative Example 23 | Comparative Example 24 | Comparative Example 25 | Comparative Example 26 | Example 12 | Example 13 |
|---|---|---|---|---|---|---|
| Increment in redness (%) | 13 | — | 27 | — | 49 | — |
| Bonding rate of split hair (%) | — | 0 | — | 35 | — | 48 |

As shown in Table 11, it was confirmed that Examples 12 and 13 including a carbodiimide-based polymer of the present invention exhibited significantly excellent dyeing and bioconjugation effects compared to Comparative Examples 23 to 25.

Experimental Example 7: Assessment of Dyeing and Bioconjugation Effects

Each of the shampoo compositions according to Comparative Examples 23 and 25 and Example 12 was used to wash a white yak hair tress ten times, and each of the shampoo compositions according to Comparative Examples 24 and 26 and Example 13 was used to wash thirty end-split hair strands ten times to induce surface modification, and each tress was washed three times with a 15% sodium lauryl ethyl sulfate solution (surfactant) to remove a component which was not covalently bonded but just adsorbed onto the hair. Afterward, the hair tresses thus treated were compared in terms of an increment in redness using a color meter (in the case of the yak hair) or the repairing of split hair using a microscope (in the case of the split hair), the results of which are shown in Table 11 below.

Experimental Example 8

Shampoo compositions were prepared using the same compositions as in Examples 12 to 13 except that compounds listed in Table 9 below were used instead of the carbodiimide-based compound used in Examples 12 and 13. For the shampoo compositions, a surface modification effect was assessed through the same method as in Experimental Example 7, the result of which is shown in Table 12 below.

TABLE 12

| Compound | Increment in redness (%) | Bonding rate of split hair (%) |
|---|---|---|
| 1,3-Bis(isocyanatomethyl)cyclohexane-, homopolymer, polyethylene glycol mono-Me-ether-blocked | 45 | 42 |
| Benzene-1,3-diisocyanate-, homopolymer, polyethylene glycol mono-Me-ether-blocked | 43 | 40 |

TABLE 12-continued

| Compound | Increment in redness (%) | Bonding rate of split hair (%) |
|---|---|---|
| Hexamethylene diisocyanate-, homopolymer, polyethylene glycol mono-Me-ether-blocked | 40 | 41 |
| PEG 600 diisocyanate-, homopolymer, polyethylene glycol mono-Me-ether-blocked | 47 | 46 |
| Diphenylmethane-2,2'-diisocyanate-, homopolymer, polyethylene glycol mono-Me-ether-blocked | 45 | 45 |
| Isophorone diisocyanate-, homopolymer, polyethylene glycol mono-Me-ether-blocked | 42 | 43 |

Comparative Examples 27 to 32 and Examples 14 to 16: Preparation of Fabric Detergent Composition Compositions for a fabric detergent, which contain stearyl amidopropyl amine, amodimethicone, or mono-(6-ethanediamine-6-deoxy)-beta-cyclodextrin, which is generally used in a liquid laundry detergent as a component for preventing static electricity, a component for softening a fabric, or a component for removing an odor, respectively, in compositions and quantities as listed in Table 13 below, and include no carbodiimide-based polymer (Comparative Examples 27 to 29); benzene, 1,3-bis(1-isocyanato-1-methylethyl)-, homopolymer, polyethylene glycol mono-Me-ether-blocked as a carbodiimide-based polymer (Comparative Examples 30 to 32); or 1,1'-methylene-bis-(3-isocyanatocyclohexane)-, homopolymer, polyethylene glycol mono-Me-ether-blocked polymer which is a carbodiimide-based polymer of the present invention (Examples 14 to 16), were prepared.

TABLE 13

| Composition (wt %) | Comparative Example 27 | Comparative Example 28 | Comparative Example 29 | Comparative Example 30 | Comparative Example 31 | Comparative Example 32 | Example 14 | Example 15 | Example 16 |
|---|---|---|---|---|---|---|---|---|---|
| Water | 57.1 | 57.1 | 57.1 | 56.1 | 56.1 | 56.1 | 56.1 | 56.1 | 56.1 |
| Lauryl sulfate | 20.0 | 20.0 | 20.0 | 20.0 | 20.0 | 20.0 | 20.0 | 20.0 | 20.0 |
| Laurylalcohol ethoxylate (12 moles) | 7.00 | 7.00 | 7.00 | 7.00 | 7.00 | 7.00 | 7.00 | 7.00 | 7.00 |
| Lauric acid | 4.0 | 4.0 | 4.0 | 4.0 | 4.0 | 4.0 | 4.0 | 4.0 | 4.0 |
| Sodium triphosphate | 10.0 | 10.0 | 10.0 | 10.0 | 10.0 | 10.0 | 10.0 | 10.0 | 10.0 |
| Fragrance | 0.9 | 0.9 | 0.9 | 0.9 | 0.9 | 0.9 | 0.9 | 0.9 | 0.9 |
| Stearyl amidopropyl amine | 1.0 | — | — | 1.0 | — | — | 1.0 | — | — |
| Amodimethicone | — | 1.0 | — | — | 1.0 | — | — | 1.0 | — |
| Mono-(6-ethanediamie-6-ndeoxy)-beta-cyclodextrin | — | — | 1.0 | — | — | 1.0 | — | — | 1.0 |
| Benzene,1,3-bis(1-isocyanato-1-methylethyl) homopolymer, polyethylene glycol mono-Me-ether-blocked | — | — | — | 1.0 | 1.0 | 1.0 | — | — | — |
| 1,1'-methylene-bis-(3-isocyanatocyclohexane)-, homopolymer, polyethylene glycol mono-Me-ether-blocked | — | — | — | — | — | — | 1.0 | 1.0 | 1.0 |
| Total | 100.0 | 100.0 | 100.0 | 100.0 | 100.0 | 100.0 | 100.0 | 100.0 | 100.0 |

Experimental Example 9: Assessment of Effects of Preventing Static Electricity, Softening Fabric, and Removing Odor The detergent compositions according to Comparative Examples 27 to 32 and Examples 14 to 16 were used to wash a standard wool fabric with a size of 5 cm (width)×5 cm (length) ten times to induce surface modification, and each wool fabric was washed three times with a 15% sodium lauryl ethyl sulfate solution (surfactant) to remove a component for preventing static electricity, softening a fabric, or removing an odor, which was not covalently bonded but just adsorbed onto the fabric. Afterward, the wool fabrics thus treated were compared in terms of effects of preventing static electricity, softening a fabric, and removing an odor (sensory evaluation; five-level scale [5: very good, 4: slightly good, 3: moderate, 2: slightly poor, 1: very poor]; n=30), the result of which is shown in Table 14 below.

TABLE 14

| Classification | Comparative Example 27 | Comparative Example 28 | Comparative Example 29 | Comparative Example 30 | Comparative Example 31 | Comparative Example 32 | Example 14 | Example 15 | Example 16 |
|---|---|---|---|---|---|---|---|---|---|
| Static electricity prevention rate (%) | 10.2 | — | — | 38.6 | — | — | 52.4 | — | — |
| Softening effect (sensibility, five-level scale) | — | 2.7 | — | — | 3.9 | — | — | 4.3 | — |
| Odor removal (sense, five-level scale) | — | — | 2.5 | — | — | 3.9 | — | — | 4.5 |

As shown in Table 14, it was confirmed that Examples 14 to 16 including a carbodiimide-based polymer of the present invention exhibited significantly excellent effects of preventing static electricity, softening a fabric, and removing an odor compared to Comparative Examples 27 to 32.

Experimental Example 10

Detergent compositions were prepared using the same compositions as in Examples 14 to 16 except that compounds listed in Table 9 below were used instead of the carbodiimide-based compound used in Examples 14 to 16. For the detergent compositions, a surface modification effect was assessed through the same method as in Experimental Example 9, the result of which is shown in Table 15 below.

TABLE 15

| Compound | Static electricity prevention rate (%) | Softening effect (sensibility, five-level scale) | Odor removal (sense, five-level scale) |
|---|---|---|---|
| 1,3-Bis(isocyanatomethyl)cyclohexane-, homopolymer, polyethylene glycol mono-Me-ether-blocked | 50.6 | 4.1 | 4.3 |
| Benzene-1,3-diisocyanate-, homopolymer, polyethylene glycol mono-Me-ether-blocked | 48.2 | 4.1 | 4.2 |
| Hexamethylene diisocyanate-, homopolymer, polyethylene glycol mono-Me-ether-blocked | 45.3 | 4.0 | 4.0 |
| PEG 600 diisocyanate-, homopolymer, polyethylene glycol mono-Me-ether-blocked | 50.1 | 4.2 | 4.4 |
| Diphenylmethane-2,2'-diisocyanate-, homopolymer, polyethylene glycol mono-Me-ether-blocked | 49.6 | 4.2 | 4.1 |
| Isophorone diisocyanate-, homopolymer, polyethylene glycol mono-Me-ether-blocked | 48.7 | 4.1 | 4.2 |

Preparation Example 1: Preparation of Body Cleanser

Body cleansers as shown in Table 16 below were prepared through a common method of preparing a body cleanser.

TABLE 16

| Composition | Conditioning body cleanser | Skin gloss body cleanser | Moisturizing body cleanser | Dyeing body cleanser | Whitening body cleanser | Wrinkle care body cleanser | Keratin care body cleanser |
|---|---|---|---|---|---|---|---|
| Raw material | Content (%) | Content (%) | Content (%) | Content (%) | Content (%) | Content (%) | Content (%) |

TABLE 16-continued

| Composition | Conditioning body cleanser | Skin gloss body cleanser | Moisturizing body cleanser | Dyeing body cleanser | Whitening body cleanser | Wrinkle care body cleanser | Keratin care body cleanser |
|---|---|---|---|---|---|---|---|
| Water | 52.5 | 52.5 | 53 | 54.5 | 52.5 | 53 | 52.5 |
| Polyquaternium-7 | 0.5 | 0.5 | 0.5 | 0.5 | 0.5 | 0.5 | 0.5 |
| EDTA 4Na | 0.1 | 0.1 | 0.1 | 0.1 | 0.1 | 0.1 | 0.1 |
| Lauric acid | 3.0 | 3.0 | 3.0 | 3.0 | 3.0 | 3.0 | 3.0 |
| Myristic acid | 4.0 | 4.0 | 4.0 | 4.0 | 4.0 | 4.0 | 4.0 |
| Sodium lauryl ether (2 moles) sulfate (30%) | 20.0 | 20.0 | 20.0 | 20.0 | 20.0 | 20.0 | 20.0 |
| Cocamidopropyl betaine (30%) | 15.0 | 15.0 | 15.0 | 15.0 | 15.0 | 15.0 | 15.0 |
| Fragrance | 0.9 | 0.9 | 0.9 | 0.9 | 0.9 | 0.9 | 0.9 |
| Sphingosine | 2.0 | — | — | — | — | — | — |
| Amodimethicone | — | 2.0 | — | — | — | — | — |
| Red No. 227 | — | — | — | 0.2 | — | — | — |
| Niacinamide | — | — | — | — | 2.0 | — | — |
| Hyaluronic acid | 0.5 | 0.5 | 2.0 | 0.5 | 0.5 | 2.0 | 0.5 |
| Salicylic acid | — | — | — | — | — | — | 2.0 |
| 1,1'-methylene-bis-(3-isocyanatocyclohexane)-, homopolymer, polyethylene glycol mono-Me-ether-blocked | 1.0 | 1.0 | 1.0 | 1.0 | 1.0 | 1.0 | 1.0 |
| pH controlling agent | Suitable amount | Suitable amount | Suitable amount | Suitable amount | Suitable amount | Suitable amount | Suitable amount |
| Total | 100.0 | 100.0 | 100.0 | 100.0 | 100.0 | 100.0 | 100.0 |

Preparation Example 2: Preparation of Skin Care Products (Whitening Mist, Lotion, Cream, and Pack)

Each of a mist, a lotion, a cream, and a pack as shown in Table 17 below was prepared through common methods of preparing a mist, a lotion, a cream, and a pack.

TABLE 17

| Composition (wt %) | Whitening mist | Whitening lotion | Whitening cream | Whitening pack |
|---|---|---|---|---|
| Niacinamide | 2.0 | 2.0 | 2.0 | 2.0 |
| 1,1'-methylene-bis-(3-isocyanatocyclohexane)-, homopolymer, polyethylene glycol mono-Me-ether-blocked | 1.0 | 1.0 | 1.0 | 1.0 |
| Glycerine | 3.0 | 3.0 | 3.0 | 3.0 |
| Butylene glycol | 3.0 | 3.0 | 3.0 | — |
| Propylene glycol | 3.0 | 3.0 | — | — |
| Carboxyvinyl polymer | 0.1 | 0.1 | 0.1 | — |
| Polyvinyl alcohol | — | — | — | 15.0 |
| PEG-12 nonyl phenyl ether | 0.3 | — | — | 0.5 |
| Polysorbate 80 | 0.5 | — | — | — |
| Polysorbate 60 | — | 1.5 | 1.5 | 1.5 |
| Sorbitan sesquioleate | — | 1.5 | — | — |
| Sorbitan stearate | — | — | 0.5 | — |
| Liquid paraffin | — | 0.5 | 10.0 | — |
| Caprylic/capric triglyceride | — | 5.0 | 5.0 | — |
| Squalane | — | 5.0 | 5.0 | — |
| Cetearyl glucoside | — | — | 2.0 | — |
| Ethanol | 10.0 | — | — | — |
| Triethanolamine | 0.1 | 0.1 | 0.1 | — |
| Stearyl alcohol | — | 1.0 | — | — |
| Beeswax | — | 5.0 | — | — |
| Preservative | Suitable amount | Suitable amount | Suitable amount | Suitable amount |
| Fragrance | Suitable amount | Suitable amount | Suitable amount | Suitable amount |
| Purified water buffer (pH 5.5) | Remainder | Remainder | Remainder | Remainder |
| Total | 100.0 | 100.0 | 100.0 | 100.0 |

Preparation Example 3: Preparation of Conditioning Shampoo

A hair conditioning shampoo as shown in Table 18 below was prepared through a common method of preparing a hair shampoo.

TABLE 18

| Raw material | Content |
|---|---|
| Water | 44.6 |
| Polyquaternium-10 | 0.5 |
| EDTA 4Na | 0.05 |
| Sodium lauryl ether (2 moles) sulfate (30%) | 35.0 |
| Cocamidopropyl betaine (30%) | 15.0 |
| Fragrance | 0.9 |
| Stearyl amidopropyl amine | 1.0 |
| 1,1'-methylene-bis-(3-isocyanatocyclohexane)-, homopolymer, polyethylene glycol mono-Me-ether-blocked | 1.0 |
| pH controlling agent | Suitable amount |
| Total | 100.0 |

Preparation Example 4: Preparation of Hair Product (Conditioning Mist, Lotion, Cream, and Pack)

Hair conditioning products as shown in Table 19 below were prepared through common methods of preparing a hair conditioning mist, lotion, cream, and pack.

TABLE 19

| Composition (wt %) | Conditioning mist | Conditioning lotion | Conditioning cream | Conditioning pack |
|---|---|---|---|---|
| Stearyl amidopropyl amine | 1 | 1 | 1 | 1 |
| Phenyl amodimethicone | 1 | 1 | 1 | 1 |
| Polylysine | 1 | 1 | 1 | 1 |
| Chitosan polymer | 1 | 1 | 1 | 1 |
| 1,1'-methylene-bis-(3-isocyanatocyclohexane)-, homopolymer, polyethylene glycol mono-Me-ether-blocked | 1 | 1 | 1 | 1 |
| Glycerine | 3 | 3 | 3 | 3 |
| Butylene glycol | 3 | 3 | 3 | — |
| Propylene glycol | 3 | 3 | — | — |
| Carboxyvinyl polymer | 0.1 | 0.1 | 0.1 | — |
| Polyvinyl alcohol | — | — | — | 15 |
| PEG-12 nonyl phenyl ether | 0.3 | — | — | 0.5 |
| Polysorbate 80 | 0.5 | — | — | — |
| Polysorbate 60 | — | 1.5 | 1.5 | 1.5 |
| Sorbitan sesquioleate | — | 1.5 | — | — |
| Sorbitan stearate | — | — | 0.5 | — |
| Liquid paraffin | — | 0.5 | 10 | — |
| Caprylic/capric triglyceride | — | 5 | 5 | — |
| Squalane | — | 5 | 5 | — |
| Cetearyl glucoside | — | — | 2 | — |
| Ethanol | 10 | — | — | — |
| Triethanolamine | 0.1 | 0.1 | 0.1 | — |
| Stearyl alcohol | — | 1 | — | — |
| Beeswax | — | 5 | — | — |
| Preservative | Suitable amount | Suitable amount | Suitable amount | Suitable amount |
| Fragrance | Suitable amount | Suitable amount | Suitable amount | Suitable amount |
| Purified water buffer (pH 4.5) | Remainder | Remainder | Remainder | Remainder |

Preparation Example 5: Preparation of Laundry Detergent

A laundry detergent as shown in Table 20 below was prepared through a common method of preparing a laundry detergent.

TABLE 20

| Raw material | Content (%) |
|---|---|
| Water | 54.1 |
| Lauryl sulfate | 20.0 |
| Laurylalcohol ethoxylate (12 moles) | 7.00 |
| Lauric acid | 4.0 |
| Sodium triphosphate | 10.0 |
| Fragrance | 0.9 |
| Stearyl amidopropyl amine | 1.0 |
| Amodimethicone | 1.0 |
| mono-(6-ethanediamine-6-deoxy)-beta-cyclodextrin | 1.0 |
| 1,1'-methylene-bis-(3-isocyanatocyclohexane)-, homopolymer, polyethylene glycol mono-Me-ether-blocked | 1.0 |
| Total | 100.0 |

Preparation Example 6: Preparation of Fabric Softener

A laundry softener as shown in Table 21 below was prepared through a common method of preparing a fabric softener.

TABLE 21

| Raw material | Content (%) |
|---|---|
| Water | 88 |
| Isostearyl amine | 0.5 |
| Distearyl dimethylammonium chloride | 5.0 |
| Stearyl amidopropyl amine | 1.0 |
| Amodimethicone | 1.0 |
| mono-(6-ethanediamine-6-deoxy)-beta-cyclodextrin | 1.0 |
| 1,1'-methylene-bis-(3-isocyanatocyclohexane)-, homopolymer, polyethylene glycol mono-Me-ether-blocked | 1.0 |
| Ethanol | 1.0 |
| Preservative, Antimicrobial agent | Suitable amount |
| Fragrance | Suitable amount |
| Total | 100.0 |

A composition for surface modification according to the present invention includes a reactive surface-modifying component (or a reactive fabric care component) including a specific functional group capable of covalently bonding with a protein residue of skin, hair, or a fabric and/or a specific carbodiimide-based compound so that covalent bonding is formed without causing damage to skin, hair, or a fabric, and thus a skin or hair surface modification effect or a fabric care effect can be semi-permanently provided.

While the invention has been shown and described with reference to certain exemplary embodiments thereof, it will be understood by those skilled in the art that various changes in form and details may be made therein without departing from the spirit and scope of the invention as defined by the appended claims.

The invention claimed is:

1. A method for modifying the surface of hair or skin, comprising preparing a composition comprising a carbodiimide-based compound represented by Chemical Formula 1 or a salt form thereof formed by bonding with a metal ion, and a hair-modifying component or a skin-modifying component, wherein the hair-modifying component or the skin-modifying component has a carboxyl group;

forming a reactive ester by a reaction between the carbodiimide-based compound and the hair-modifying component or the skin-modifying component; and forming a covalent bond by a reaction between the formed reactive ester and a biological amino acid having an amine group in a hair or a skin protein surface:

[Chemical Formula 1]

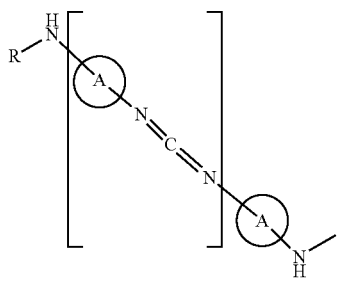

wherein A each independently represents a monomer selected from structures listed below, R is the same in each occurrence, and each represents hydrogen; a C1 to C500 linear, branched, or cyclic hydrocarbon moiety; or an aromatic hydrocarbon moiety, wherein the linear, branched, cyclic or aromatic hydrocarbon moiety includes a double bond, or is optionally substituted with one or more elements selected from the group consisting of O, N, S, P, and Si, m is an integer ranging from 1 to 100,

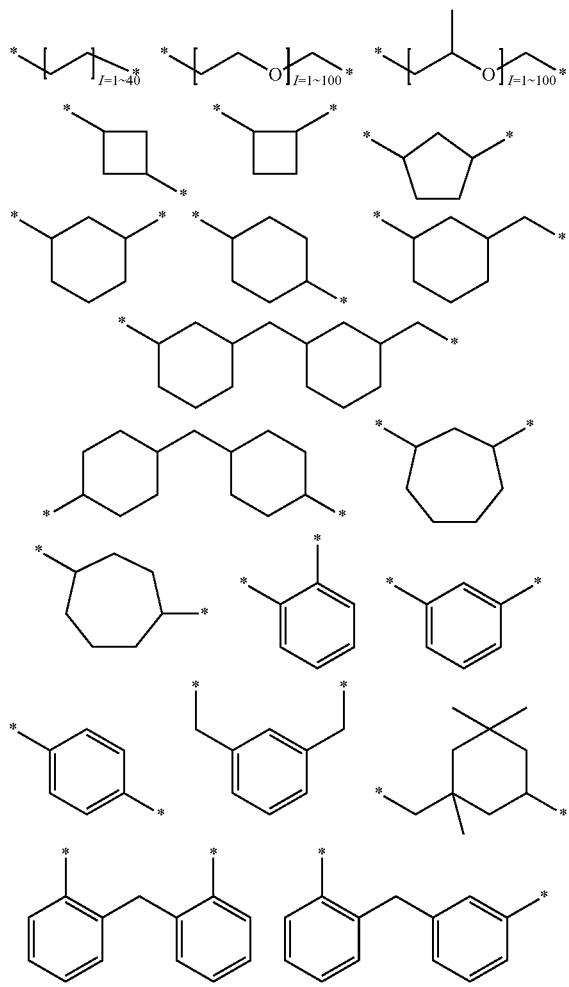

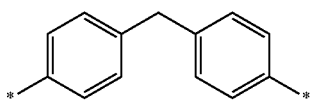

wherein * denotes a connecting position.

2. The method for modifying the surface of hair or skin according to claim 1, wherein the carbodiimide-based compound is represented by Chemical Formula 2:

[Chemical Formula 2]

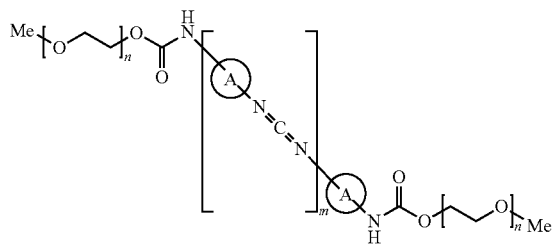

wherein A each independently represents a monomer selected from structures listed below, m is an integer ranging from 1 to 100, and n is an integer ranging from 1 to 1,000,

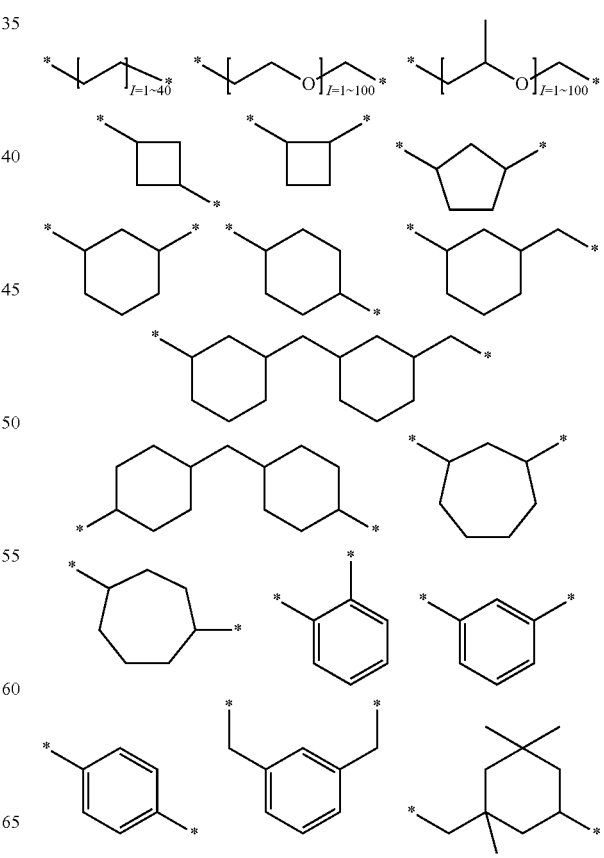

-continued

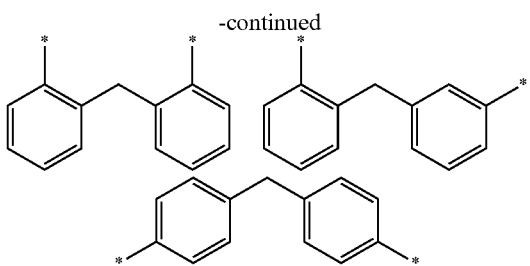

wherein * denotes a connecting position.

3. A method for modifying the surface of hair or skin, comprising
preparing a composition comprising a carbodiimide-based compound represented by Chemical Formula 3, and a hair-modifying component or a skin-modifying component, wherein the hair-modifying component or the skin-modifying component has a carboxyl group;
forming a reactive ester by a reaction between the carbodiimide-based compound and the hair-modifying component or the skin-modifying component; and
forming a covalent bond by a reaction between the formed reactive ester and a biological amino acid having an amine group in a hair or a skin protein surface:

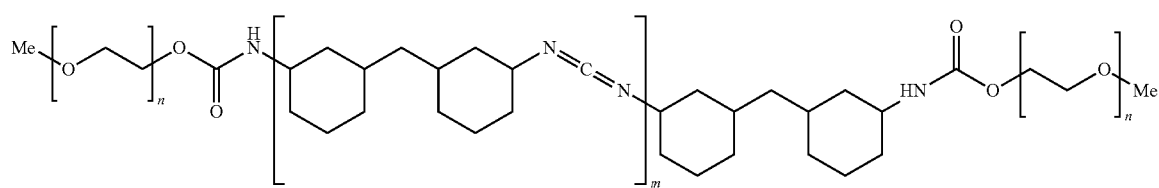

wherein n is an integer ranging from 1 to 130, and m is an integer ranging from 1 to 20.

4. A method for modifying the surface of hair or skin, comprising
preparing a composition comprising a carbodiimide-based compound represented by Chemical Formula 1 or a salt form thereof formed by bonding with a metal ion, and a hair-modifying component or a skin-modifying component, wherein the hair-modifying component or the skin-modifying component has an amine group;
forming a reactive ester by a reaction between a biological amino acid having a carboxyl group in a hair or a skin protein surface and the carbodiimide-based compound, and
forming a covalent bond by a reaction between the formed reactive ester and the hair-modifying component or the skin-modifying component:

[Chemical Formula 1]

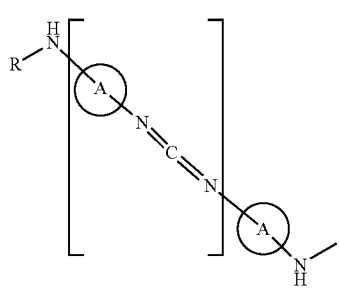

wherein A each independently represents a monomer selected from structures listed below,
R is the same in each occurrence, and each represents hydrogen; a C1 to C500 linear, branched, or cyclic hydrocarbon moiety; or an aromatic hydrocarbon moiety, wherein the linear, branched, cyclic or aromatic hydrocarbon moiety includes a double bond, or is optionally substituted with one or more elements selected from the group consisting of O, N, S, P, and Si,
m is an integer ranging from 1 to 100,

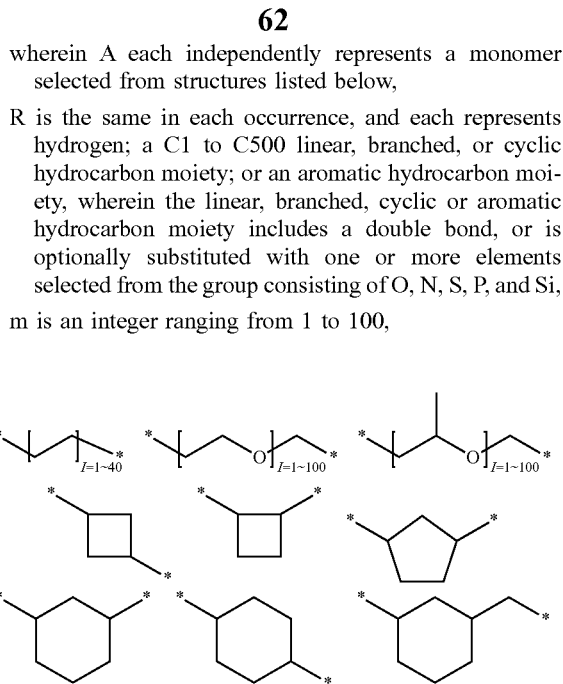

[Chemical Formula 3]

-continued

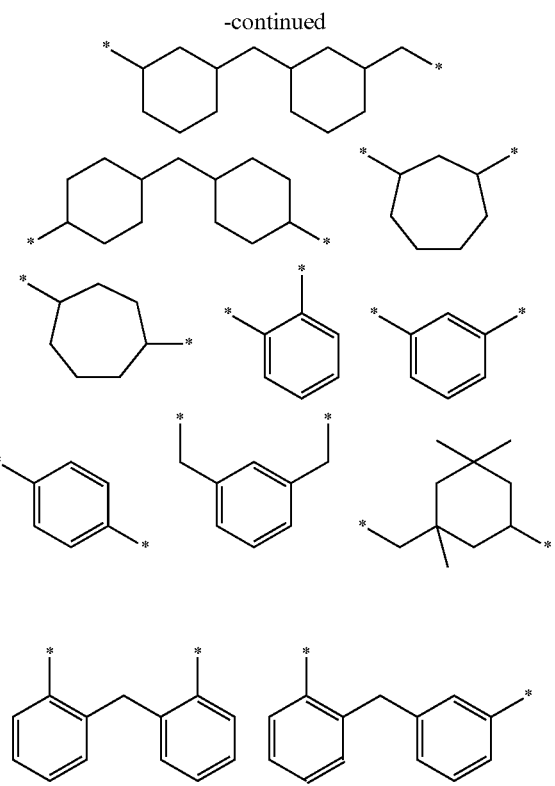

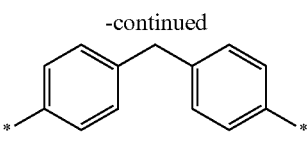

wherein * denotes a connecting position.

5. The method for modifying the surface of hair or skin according to claim 4,
wherein the carbodiimide-based compound is a represented by Chemical Formula 2:

[Chemical Formula 2]

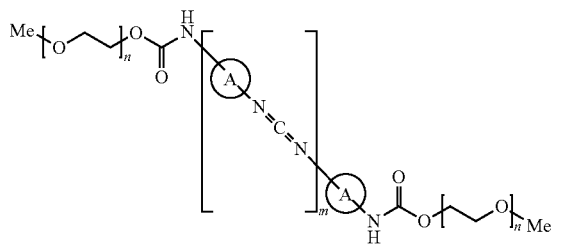

wherein A each independently represents a monomer selected from structures listed below,
m is an integer ranging from 1 to 100, and
n is an integer ranging from 1 to 1,000,

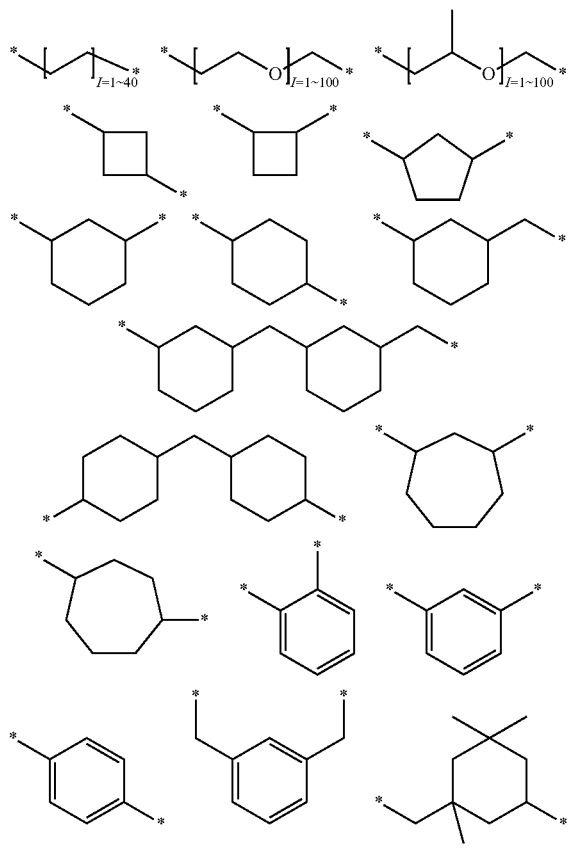

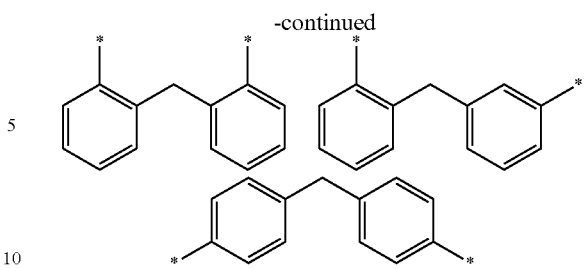

wherein * denotes a connecting position.

6. The method for modifying the surface of hair or skin according to claim 4,
wherein the carbodiimide-based compound is represented by Chemical Formula 3:

[Chemical Formula 3]

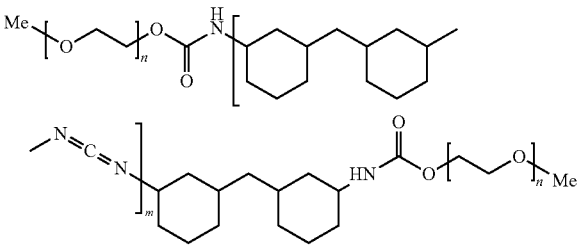

wherein n is an integer ranging from 1 to 130, and m is an integer ranging from 1 to 20.

7. The method for modifying the surface of hair or skin according to claim 1, wherein the hair-modifying component is a component for antioxidation; conditioning; blocking ultraviolet rays; imparting fragrance; applying a dye; bioconjugation; inhibiting bacteria; stimulating hair growth; or stimulating hair regrowth, and the skin-modifying component is a component for antioxidation; conditioning; moisturizing; whitening; blocking ultraviolet rays; imparting fragrance; preventing or improving a wrinkle; keratin care; preventing or improving dandruff/itching; stimulating hair growth; preventing acne or inhibiting bacteria; suppressing body odor; atopic dermatitis care; pore care; epilation; fingernail and toenail care; or bioconjugation, or a component in the form of a dye or a powder.

8. The method for modifying the surface of hair or skin according to claim 1, wherein the hair-modifying component or the skin-modifying component has a functional group capable of covalently bonding with a protein residue in the hair or skin protein surface.

9. The method for modifying the surface of hair or skin according to claim 8, wherein the functional group capable of covalently bonding with a protein residue is one or more selected from the group consisting of imidoesters, aryl azides, diazirines, hydroxymethyl phosphine, pentafluorophenyl esters, pyridyl disulfide, sulfo-hydroxysuccinimide esters, alkoxyamines, hydrazides, haloacetyls, azide, carbonates, aldehydes, propionaldehyde, butylaldehyde, nitrophenyl carbonate, aziridines, isocyanate, thiocyanate, epoxides, tresylates, succinimide, hydroxysuccinimidyl esters, imidazole, oxycarbonylamidazole, imines, thiols, maleimide, vinyl sulfone, ethyleneimine, thioethers, acrylonitrile, acrylic or methacrylic acid ester, disulfides, and ketones.

10. The method for modifying the surface of hair or skin according to claim 1, wherein the carbodiimide-based compound is comprised at a content of 0.0001 to 10 parts by weight with respect to 100 parts by weight of the composition.

11. The method for modifying the surface of hair or skin according to claim 1, wherein the composition is prepared in the form of a single formulation in which the carbodiimide-based compound and the hair-modifying component or the skin-modifying component are encapsulated; or in the form of two distinct formulations in which the carbodiimide-based compound and the hair-modifying component or the skin-modifying component are separated from each other.

12. The method for modifying the surface of hair or skin according to claim 3, wherein the hair-modifying component is a component for antioxidation; conditioning; blocking ultraviolet rays; imparting fragrance; applying a dye; bioconjugation; inhibiting bacteria; stimulating hair growth; or stimulating hair regrowth, and the skin-modifying component is a component for antioxidation; conditioning; moisturizing; whitening; blocking ultraviolet rays; imparting fragrance; preventing or improving a wrinkle; keratin care; preventing or improving dandruff/itching; stimulating hair growth; preventing acne or inhibiting bacteria; suppressing body odor; atopic dermatitis care; pore care; epilation; fingernail and toenail care; or bioconjugation, or a component in the form of a dye or a powder.

13. The method for modifying the surface of hair or skin according to claim 3, wherein the hair-modifying component or the skin-modifying component has a functional group capable of covalently bonding with a protein residue in the hair or skin protein surface.

14. The method for modifying the surface of hair or skin according to claim 13, wherein the functional group capable of covalently bonding with a protein residue is one or more selected from the group consisting of imidoesters, aryl azides, diazirines, hydroxymethyl phosphine, pentafluorophenyl esters, pyridyl disulfide, sulfo-hydroxysuccinimide esters, alkoxyamines, hydrazides, haloacetyls, azide, carbonates, aldehydes, propionaldehyde, butylaldehyde, nitrophenyl carbonate, aziridines, isocyanate, thiocyanate, epoxides, tresylates, succinimide, hydroxysuccinimidyl esters, imidazole, oxycarbonylamidazole, imines, thiols, maleimide, vinyl sulfone, ethyleneimine, thioethers, acrylonitrile, acrylic or methacrylic acid ester, disulfides, and ketones.

15. The method for modifying the surface of hair or skin according to claim 3, wherein the carbodiimide-based compound is comprised at a content of 0.0001 to 10 parts by weight with respect to 100 parts by weight of the composition.

16. The method for modifying the surface of hair or skin according to claim 3, wherein the composition is prepared in the form of a single formulation in which the carbodiimide-based compound and the hair-modifying component or the skin-modifying component are encapsulated; or in the form of two distinct formulations in which the carbodiimide-based compound and the hair-modifying component or the skin-modifying component are separated from each other.

17. The method for modifying the surface of hair or skin according to claim 4, wherein the hair-modifying component or the skin-modifying component has a functional group capable of covalently bonding with a protein residue in the hair or skin protein surface.

18. The method for modifying the surface of hair or skin according to claim 17, wherein the functional group capable of covalently bonding with a protein residue is one or more selected from the group consisting of imidoesters, aryl azides, diazirines, hydroxymethyl phosphine, pentafluorophenyl esters, pyridyl disulfide, sulfo-hydroxysuccinimide esters, alkoxyamines, hydrazides, haloacetyls, azide, carbonates, aldehydes, propionaldehyde, butylaldehyde, nitrophenyl carbonate, aziridines, isocyanate, thiocyanate, epoxides, tresylates, succinimide, hydroxysuccinimidyl esters, imidazole, oxycarbonylamidazole, imines, thiols, maleimide, vinyl sulfone, ethyleneimine, thioethers, acrylonitrile, acrylic or methacrylic acid ester, disulfides, and ketones.

19. The method for modifying the surface of hair or skin according to claim 4, wherein the carbodiimide-based compound is comprised at a content of 0.0001 to 10 parts by weight with respect to 100 parts by weight of the composition.

20. The method for modifying the surface of hair or skin according to claim 4, wherein the composition is prepared in the form of a single formulation in which the carbodiimide-based compound and the hair-modifying component or the skin-modifying component are encapsulated; or in the form of two distinct formulations in which the carbodiimide-based compound and the hair-modifying component or the skin-modifying component are separated from each other.

* * * * *